(12) United States Patent
Klingler et al.

(10) Patent No.: US 6,500,803 B1
(45) Date of Patent: Dec. 31, 2002

(54) FACTOR VIIA INHIBITORS

(75) Inventors: Otmar Klingler, Rodgau (DE); Manfred Schudok, Eppstein/Ts. (DE); Gerhard Zoller, Schöneck (DE); Uwe Heinelt, Wiesbaden (DE); Elisabeth Defossa, Idstein (DE); Hans Matter, Langenselbold (DE); Pavel Safar, Tucson, AZ (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/588,651

(22) Filed: Jun. 7, 2000

(30) Foreign Application Priority Data

Jun. 8, 1999  (EP) ............................................. 99111109

(51) Int. Cl.$^7$ ............................................. A61K 38/05
(52) U.S. Cl. ........................... 514/19; 530/331; 514/18; 562/445
(58) Field of Search ..................... 514/18, 19; 530/331; 562/445

(56) References Cited

FOREIGN PATENT DOCUMENTS

| | | |
|---|---|---|
| DE | 0 987274 | 3/2000 |
| WO | WO 89/09612 | 10/1989 |
| WO | WO 92/06711 | 4/1992 |
| WO | WO 95/29189 | 11/1995 |
| WO | WO 96/12800 | 5/1996 |
| WO | WO 97/47651 | 12/1997 |

OTHER PUBLICATIONS

Steinmetzer, T. Expert Opinion on Investigational Drugs, 10 845–64, 2001.*
Rutsch, W. European Heart Journal 19 Suppl K, K11–K17, 1998.*
Oldgren J. European Heart Journal 20 1657–66, 1999.*
G.J. Broze, Jr., Tissue factor pathway inhibitor and the current concept of blood coagulation, *Blood Coagulation and Fibrinolysis* 6 (Suppl. 1):S7–S13 (1995).
H. Bundgaard, Novel chemical approaches in prodrug design, *Drugs of the Future* 16(5):443–458 (1991).
Y. Cheng et al., Relationship Between The Inhibition Constant ($K_1$) and the Concentration of Inhibitor Which Causes 50 Per Cent Inhibition ($I_{50}$) of an Enzymatic Reaction, *Biochemical Pharmacology* 22:3099–3108 (1973).
H. Cole, The tissue factor pathway of coagulation, *Australian Journal of Medical Science* 16:87–93 (1995).
D. Fleisher et al., Improved oral drug delivery: solubility limitations overcome by the use of produgs, *Advanced Drug Delivery Reviews* 19:115–129 (1996).
L.A. Harker et al., Antithrombotic Benefits and Hemorrhagic Risks of Direct Thrombin Antagonists, *Thrombosis and Haemostasis* 74(1):464–472 (1995).
L.A. Harker et al., Antithromboti and Antilesion Benefits without Hemorrhagic Risks by Inhibiting Tissue Factor Pathway, *Haemostasis* 26(Suppl. 1):76–82 (1996).
J.A. Ostrem et al., Discovery of a Novel, Potent, and Specific Family of Factor Xa Inhibitors via Combinatorial Chemistry, *Biochemistry* 37:1053–1059 (1998).
I.H. Segel, Enzyme Kinetics: Behavior and Analysis of Rapid Equilibrium and Steady–State Enzyme Systems, Chapter III, pp. 100–125 (John Wiley & Sons, New York 1975).
S. Wang, p–Alkoxybenzyl Alcohol Resin and p–Alkoxybenzylox yearbonylhydrazide Resin for Solid Phase Synthesis of Protected Peptide Fragments, *Journal of the American Chemical Society* 95(4):1328–1333 (1973).

\* cited by examiner

Primary Examiner—Christopher S. F. Low
Assistant Examiner—David Lukton
(74) *Attorney, Agent, or Firm*—Finnegan, Henderson, Farabow, Garrett & Dunner, LLP

(57) ABSTRACT

The present invention relates to compounds of formula I, in which $R^1$, $R^2$, $R^{91}$, $R^{92}$, $R^{93}$, $R^{94}$, $R^{95}$, $R^{96}$, $R^{97}$, r, s, and t have the meanings indicated in the claims. Compounds of formula I are valuable pharmacologically active compounds. They exhibit a strong antithrombotic effect and are suitable, for example, for the therapy and prophylaxis of thromboembolic diseases or restenoses. They are reversible inhibitors of the blood clotting enzyme factor VIIa and can in general be applied in conditions in which an undesired activity of factor VIIa is present or for the cure or prevention of conditions in which an inhibition of factor VIIa is intended. The invention furthermore relates to processes for the preparation of compounds of formula I, their use, in particular as active ingredients in pharmaceuticals, and pharmaceutical preparations comprising them.

12 Claims, No Drawings

FACTOR VIIA INHIBITORS

The present invention relates to compounds of formula I,

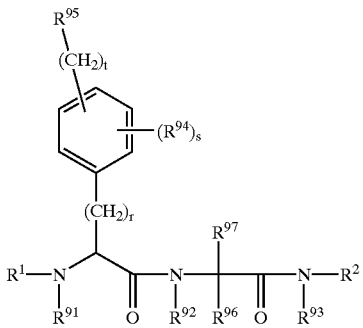

in which $R^1$, $R^2$, $R^{91}$, $R^{92}$, $R^{93}$, $R^{94}$, $R^{95}$, $R^{96}$, $R^{97}$, r, s, and t have the meanings indicated below. Compounds of formula I are valuable pharmacologically active compounds. They exhibit a strong antithrombotic effect and are suitable, for example, for the therapy and prophylaxis of thromboembolic diseases or restenoses. They are reversible inhibitors of the blood clotting enzyme factor VIIa and can in general be applied in conditions in which an undesired activity of factor VIIa is present or for the cure or prevention of conditions in which an inhibition of factor VIIa is intended. The invention further relates to processes for the preparation of compounds of formula I, their use, in particular as active ingredients in pharmaceuticals, and pharmaceutical preparations comprising them.

The ability to form blood clots is vital to survival. The formation of a blood clot or a thrombus is normally the result of tissue injury that initiates the coagulation cascade and has the effect of slowing or preventing blood flow in wound healing. Other factors that are not directly related to tissue injury like atherosclerosis and inflammation may also initiate the coagulation cascade. In general, a relationship exists between inflammation and the coagulation cascade. Inflammation mediators regulate the coagulation cascade and coagulation components influence the production and activity of inflammation mediators. However, in certain disease states the formation of blood clots within the circulatory system reaches an undesirable level and is itself the source of morbidity potentially leading to pathological consequences. It is nevertheless not desirable in such disease states to completely inhibit the blood clotting system because life threatening hemorrhage would ensue. In the treatment of such states, a well-balanced intervention into the blood clotting system is required, and there is still a need for substances exhibiting a suitable pharmacological activity for achieving such a result.

Blood coagulation is a complex process involving a progressively amplified series of enzyme activation reactions in which plasma zymogens are sequentially activated by limited proteolysis. Mechanistically, the blood coagulation cascade has been divided into intrinsic and extrinsic pathways, which converge at the activation of factor X. Subsequent generation of thrombin proceeds through a single common pathway (see Scheme 1). Present evidence suggests that the intrinsic pathway plays an important role in the maintenance and growth of fibrin formation, while the extrinsic pathway is critical in the initiation phase of blood coagulation (H. Cole, Aust. J. Med. Sci. 16 (1995) 87–93; G. J. Broze, Blood Coagulation and Fibrinolysis 6, Suppl. 1 (1995) S7–S13). It is generally accepted that blood coagulation is physically initiated upon formation of a factor VIIa/tissue factor (TF) complex. Once formed, this complex rapidly initiates coagulation by activating factors IX and X. The newly generated activated factor X, i.e., factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/TF complex (extrinsic pathway) is suppressed by a Kunitz-type protease inhibitor protein, TFPI, which, when complexed to factor Xa, can directly inhibit the proteolytic activity of factor VIIa/TF.

Scheme 1
Blood coagulation cascade

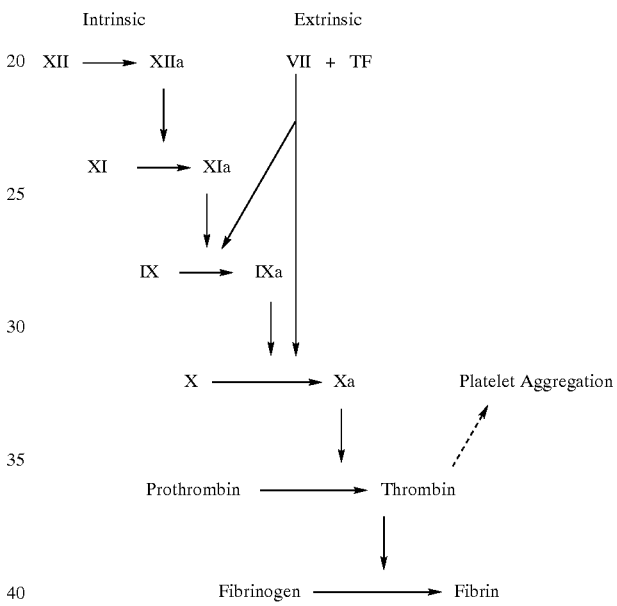

In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin. The autocatalytic nature of thrombin generation is an important safeguard against uncontrolled bleeding and it ensures that, once a given threshold level of prothrombinase is present, blood coagulation will proceed to completion. Thus, it is most desirable to develop agents that inhibit coagulation without directly inhibiting thrombin but by inhibiting other steps in the coagulation cascade like factor VIIa activity.

In many clinical applications there is a great need for the prevention of intravascular blood clots or for some anticoagulant treatment. For example, nearly 50% of patients who have undergone a total hip replacement develop deep vein thrombosis (DVT). The currently available drugs like heparin and derivatives thereof are not satisfactory in many specific clinical applications. The currently approved therapies include fixed dose low molecular weight heparin (LMWH) and variable dose heparin. Even with these drug regimes, 10% to 20% of patients develop DVT, and 5% to 10% develop bleeding complications.

Another clinical situation for which better anticoagulants are needed concerns subjects undergoing transluminal coronary angioplasty and subjects at risk for myocardial infarction or suffering from crescendo angina. The present conventionally accepted therapy, which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The widely used blood-clotting inhibitors like heparin and related sulfated polysaccharides like LMWH and heparin sulfate exert their anti-clotting effects by promoting the binding of a natural regulator of the clotting process, antithrombin III, to thrombin and to factor Xa. The inhibitory activity of heparin primarily is directed toward thrombin, which is inactivated approximately 100 times faster than factor Xa. Hirudin and hirulog are two additional thrombin-specific anticoagulants presently in clinical trials. However, these anticoagulants which inhibit thrombin also are associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors (L. A. Harker et al., *Thromb. Hemostas.* 74 (1995) 464–472). Certain peptides and peptide analogs which inhibit blood clotting by specifically inhibiting factor Xa are disclosed, for example, in WO-A-95/29189.

Specific inhibition of the factor VIIa/TF catalytic complex using monoclonal antibodies (WO-A-92/0671 1) or a protein such as chloromethyl ketone inactivated factor VIIa (WO-A-96/12800 and WO-A-97/47651) is an extremely effective means of controlling thrombus formation caused by acute arterial injury or the thrombotic complications related to bacterial septicemia. There is also experimental evidence suggesting that inhibition of factor VIIa/TF activity inhibits restenosis following balloon angioplasty (L. A. Harker et al., *Hemostasis* 26 (1996) S1:76–82). Bleeding studies have been conducted in baboons and indicate that inhibition of the factor VIIa/TF complex has the widest safety window with respect to therapeutic effectiveness and bleeding risk of any anticoagulant approach tested including thrombin, platelet, and factor Xa inhibition (L. A. Harker et al., *Thromb. Hemostas.* 74 (1995) 464–472).

A specific inhibitor of factor VIIa which has a favorable property profile would have substantial practical value in the practice of medicine. In particular, a factor VIIa inhibitor would be effective under circumstances where the present drugs of choice, like heparin and related sulfated polysaccharides, are ineffective or only marginally effective. Certain inhibitors of factor VIIa have already been described, e.g., in WO-A-89/09612. EP-A-987274 discloses compounds containing a tripeptide unit which inhibit factor VIIa. However, the property profile of these compounds is still not ideal, and there is a need for further low molecular weight factor VIIa-specific blood clotting inhibitors that are effective and do not cause unwanted side effects. The present invention satisfies this need by providing novel factor VIIa activity inhibiting compounds of formula I.

Thus, a subject of the present invention are compounds of formula I,

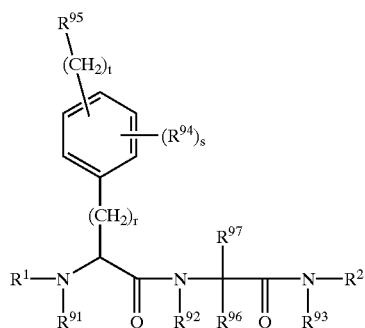

wherein:

r is 0, 1, 2, or 3;

s is 0, 1, 2, 3, or 4;

t is 0, 1, or 2;

$R^1$ is selected from hydrogen, $R^{11}$—CO—, and $R^{12}$—$SO_2$—;

$R^{11}$ is selected from hydrogen, $(C_1-C_8)$-alkyl, $(C_6-C_{14})$-aryl, $(C_6-C_{14})$-aryl-$(C_1-C_4)$-alkyl-, Het-, Het-$(C_1-C_4)$-alkyl-, $(C_1-C_8)$-alkyloxy-, $(C_6-C_{14})$-aryloxy-, $(C_6-C_{14})$-aryl-$(C_1-C_4)$-alkyloxy-, amino, $(C_1-C_8)$-alkylamino-, $(C_6-C_{14})$-arylamino-, and $(C_6-C_{14})$-aryl-$(C_1-C_4)$-alkylamino-, where all these groups are unsubstituted or substituted by one or more identical or different $R^{40}$ substituents;

$R^{12}$ is selected from $(C_1-C_8)$-alkyl, $(C_6-C_{14})$-aryl, $(C_6-C_{14})$-aryl-$(C_1-C_4)$-alkyl-, Het-, Het-$(C_1-C_4)$-alkyl-, di$((C_1-C_8)$-alkyl)amino-, and di$((C_6-C_{14})$-aryl-$(C_1-C_4)$-alkyl)amino-, where all these groups are unsubstituted or substituted by one or more identical or different $R^{40}$ substituents;

$R^2$ is hydrogen, $R^{21}(R^{22})$CH—, $R^{23}$-Het-$(CH_2)_k$—, $R^{23}(R^{24})$N—$(CH_2)_m$—D—$(CH_2)_n$—, or $R^{25}(R^{26})$N—CO—$(CH_2)_p$—D—$(CH_2)_q$—, wherein D is a divalent —$C(R^{31})(R^{32})$— residue, a divalent $(C_6-C_{14})$-arylene residue, or a divalent residue derived from an aromatic Het group containing 5 to 10 ring atoms of which 1, 2, 3, or 4 are identical or different ring heteroatoms selected from nitrogen, oxygen, and sulfur, and the numbers k, m, n, p, and q which are independent of each other and can be identical or different are 0, 1, 2, 3, 4, or 5, with the proviso that when D is —$C(R^{31})(R^{32})$—, the sum m+n cannot be 0 and the sum p+q cannot be 0;

$R^{21}$ and $R^{22}$ which are independent of each other and can be identical or different are selected from hydrogen, $(C_1-C_{12})$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different substituents selected from $R^{40}$, $(C_1-C_8)$-alkylamino-, di-$((C_1-C_8)$-alkyl)-amino-, $(C_6-C_{14})$-aryl-$(C_1-C_4)$-alkylamino-, $(C_6-C_{14})$-arylamino-, aminocarbonyl-, and aminocarbonyl-$(C_1-C_8)$-alkyl-, or $R^{21}$ and $R^{22}$ together with the carbon atom to which they are bonded form a saturated or unsaturated 3-membered to 8-membered carbocyclic ring which can be condensed to one or two ring systems which are heteroaromatic rings containing 5 to 10 ring atoms of which 1, 2, or 3 are identical or different heteroatoms selected from nitrogen, oxygen, and sulfur, and/or $(C_6-C_{10})$ carbocyclic aromatic rings, where the resulting $R^{21}(R^{22})$CH— group is unsubstituted or substituted by one or more identical or different substituents selected from $R^{40}$, $(C_1-C_8)$-alkylamino-, di-$((C_1-C_8)$-alkyl)-amino-, $(C_6-C_{14})$-aryl-$(C_1-C_4)$-alkylamino-, $(C_6-C_{14})$-arylamino-, aminocarbonyl-, and aminocarbonyl-$(C_1-C_8)$-alkyl-;

$R^{23}$ is hydrogen, $R^{27}$—$SO_2$—, or $R^{28}$—CO—;

$R^{24}$ is selected from hydrogen, $(C_1-C_8)$-alkyl, $(C_6-C_{14})$-aryl, and $(C_6-C_{14})$-aryl-$(C_1-C_4)$-alkyl-;

$R^{25}$ and $R^{26}$ which are independent of each other and can be identical or different are selected from hydrogen, $(C_1-C_8)$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different $R^{40}$ substituents;

$R^{27}$ is selected from $(C_1-C_8)$-alkyl, $(C_6-C_{14})$-aryl, $(C_6-C_{14})$-aryl-$(C_1-C_4)$-alkyl-, Het-, Het-$(C_1-C_4)$-alkyl-, amino, $(C_1-C_8)$-alkylamino-, di-$((C_1-C_8)$-alkyl)amino-, $(C_6-C_{14})$-arylamino-, and $(C_6-C_{14})$-aryl-$(C_1-C_4)$-alkylamino-, where all these groups are unsubstituted or substituted by one or more identical or different $R^{40}$ substituents;

$R^{28}$ is selected from $R^{27}$, $(C_1-C_8)$-alkyloxy-, $(C_6-C_{14})$-aryloxy-, and $(C_6-C_{14})$-aryl-$(C_1-C_4)$-alkyloxy-, where all these groups are unsubstituted or substituted by one or more identical or different $R^{40}$ substituents;

$R^{31}$ and $R^{32}$ which are independent of each other and can be identical or different are selected from hydrogen, $(C_1-C_{12})$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different $R^{40}$ substituents;

$R^{40}$ is selected from halogen, hydroxy, $(C_1-C_8)$-alkyloxy-, $(C_6-C_{14})$-aryl-$(C_1-C_8)$-alkyloxy-, $(C_6-C_{14})$-aryloxy-, $(C_1-C_8)$-alkyl, $(C_6-C_{14})$-aryl, $(C_6-C_{14})$-aryl-$(C_1-C_8)$-alkyl-, $(C_1-C_8)$-alkylsulfonyl-, trifluoromethyl, acetylamino-, amino, amidino, guanidino, oxo, nitro, and cyano, where the $R^{40}$ groups are independent of each other and can be identical or different;

$R^{91}$, $R^{92}$, and $R^{93}$ which are independent of each other and can be identical or different are selected from hydrogen, $(C_1-C_8)$-alkyl, $(C_6-C_{14})$-aryl, $(C_6-C_{14})$-aryl-$(C_1-C_4)$-alkyl-, Het-, and Het-$(C_1-C_4)$-alkyl-;

$R^{94}$ is selected from $(C_1-C_4)$-alkyl, $(C_6-C_{14})$-aryl, amino, nitro, halogen, trifluoromethyl, hydroxy, and $(C_1-C_4)$-alkyloxy-, where the $R^{94}$ groups are independent of each other and can be identical or different;

$R^{95}$ is selected from amidino, guanidino, $((C_1-C_4)$-alkyl)oxycarbonylamidino-, $((C_1-C_4)$-alkyl)oxycarbonylguanidino-, and hydroxyamidino-;

$R^{96}$ is selected from hydrogen, $R^{98}$—$(C_1-C_8)$-alkyl-, $R^{98}$—$(C_6-C_{14})$-aryl-, $R^{98}$—$(C_6-C_{14})$-aryl-$(C_1-C_4)$-alkyl-, $R^{98}$-Het-, and $R^{98}$-Het-$(C_1-C_4)$-alkyl-;

$R^{97}$ is selected from $R^{99}$—$(C_1-C_8)$-alkyl-, $R^{99}$—$(C_6-C_{14})$-aryl-, $R^{99}$—$(C_6-C_{14})$-aryl-$(C_1-C_4)$-alkyl-, $R^{99}$-Het-, and $R^{99}$-Het-$(C_1-C_4)$-alkyl-;

$R^{98}$ and $R^{99}$ which are independent of each other and can be identical or different are selected from hydroxycarbonyl-, $(C_1-C_8)$-alkyloxycarbonyl-, $(C_6-C_{14})$-aryloxycarbonyl-, $(C_6-C_{14})$-aryl-$(C_1-C_4)$-alkyloxycarbonyl-, aminocarbonyl-, $(C_1-C_8)$-alkylaminocarbonyl-, tetrazolyl, —$P(O)(OH)_2$, —$S(O)_2OH$, and —$S(O)_2NH_2$;

Het is a saturated, partially unsaturated, or aromatic monocyclic or bicyclic heterocyclic ring system containing 3 to 10 ring atoms of which 1, 2, 3, or 4 are identical or different heteroatoms selected from nitrogen, oxygen, and sulfur;

in any stereoisomeric form or mixture thereof in any ratio, or a physiologically tolerable salt thereof.

All residues which can occur several times in compounds of formula I, for example, the $R^{40}$, $R^{94}$, or Het residues, can each independently of one another have the meanings indicated, and can in each case be identical or different.

As used herein, the term alkyl is to be understood in the broadest sense to mean hydrocarbon residues which can be linear, i.e., straight-chain, or branched, and can be acyclic or cyclic residues or comprise any combination of acyclic and cyclic subunits. Further, the term alkyl as used herein expressly includes saturated groups as well as unsaturated groups which latter groups contain one or more, for example, one, two, or three, double bonds and/or triple bonds, provided that the double bonds are not located within a cyclic alkyl group in such a manner that an aromatic system results. All these statements also apply if an alkyl group carries substituents or occurs as a substituent on another residue, for example, in an alkyloxy residue, an alkyloxycarbonyl residue, or an arylalkyl residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl (=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, cyclohexylmethyl-, cycloheptylmethyl-, cyclooctylmethyl-, 1-cyclopropylethyl-, 1-cyclobutylethyl-, 1-cyclopentylethyl-, 1-cyclohexylethyl-, 1-cycloheptylethyl-, 1-cyclooctylethyl-, 2-cyclopropylethyl-, 2-cyclobutylethyl-, 2-cyclopentylethyl-, 2-cyclohexylethyl-, 2-cycloheptylethyl-, 2-cyclooctylethyl-, 3-cyclopropylpropyl-, 3-cyclobutylpropyl-, 3-cyclopentylpropyl-, 3-cyclohexylpropyl-, 3-cycloheptylpropyl-, or 3-cyclooctylpropyl- in which groups the cycloalkyl subgroup as well as acyclic subgroup also can be unsaturated and/or substituted.

Of course, a cyclic alkyl group has to contain at least three carbon atoms and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_8)$-cycloalkyl, cycloalkyl-alkyl groups like $(C_3-C_7)$-cycloalkyl-$(C_1-C_5)$-alkyl- wherein the total number of carbon atoms can range from 4 to 8, and unsaturated ($C_2$–$C_8$)-alkyl like ($C_2$–$C_8$)-alkenyl or ($C_2$–$C_8$)-alkynyl. Similarly, a group like ($C_1$–$C_4$)-alkyl is to be understood as comprising, among others, saturated acyclic ($C_1$–$C_4$)-alkyl, ($C_3$–$C_4$)-cycloalkyl, cyclopropyl-methyl-, and unsaturated ($C_2$–$C_4$)-alkyl like ($C_2$–$C_4$)-alkenyl or ($C_2$–$C_4$)-alkynyl.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like ($C_2$–$C_6$)-alkenyl and ($C_2$–$C_6$)-alkynyl, and cyclic alkyl groups containing from 3 to 8 ring carbon atoms, in particular from 3 to 6 ring carbon atoms. A particular group of saturated acyclic alkyl residues is formed by ($C_1$–$C_4$)-alkyl residues like methyl, ethyl, n-propyl, isopropyl, n-butyl, isobutyl, sec-butyl, and tert-butyl.

The above statements relating to alkyl groups do not only apply to monovalent residues but correspondingly to divalent residues like alkanediyl groups, alkylene groups, or polymethylene groups examples of which are methylene, 1,2-ethylene (=ethane-1,2-diyl), 1,1-ethylene (=1-methyl-methylene), 1-isobutyl-methylene, 1,3-propylene, 2,2-dimethyl-1,3-propylene, 1,4-butylene, but-2-en-1,4-diyl, 1,2-cyclopropylene, 1,2-cyclohexylene, 1,3-cyclohexylene, or 1,4-cyclohexylene.

Unless stated otherwise, and irrespective of any specific substituents bonded to alkyl groups which are indicated in the definition of compounds of formula I, alkyl groups can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen atoms, in particular fluorine atoms.

Examples of substituted cycloalkyl groups are cycloalkyl groups which carry as substituent one or more, for example, one, two, three, or four, identical or different acyclic alkyl groups, for example, acyclic ($C_1$–$C_4$)-alkyl groups like methyl groups. Examples of substituted cycloalkyl groups are 4-methylcyclohexyl, 4-tert-butylcyclohexyl, or 2,3-dimethylcyclopentyl.

The term aryl refers to a monocyclic or polycyclic hydrocarbon residue in which at least one carbocyclic ring is present that has a conjugated pi electron system. In a ($C_6$–$C_{14}$)-aryl residue from 6 to 14 ring carbon atoms are present. Examples of ($C_6$–$C_{14}$)-aryl residues are phenyl, naphthyl, biphenylyl, fluorenyl, or anthracenyl. Examples of ($C_6$–$C_{10}$)-aryl residues are phenyl or naphthyl. Unless stated otherwise, and irrespective of any specific substituents bonded to aryl groups which are indicated in the definition of compounds of formula I, aryl residues including, for example, phenyl, naphthyl, and fluorenyl, can in general be unsubstituted or substituted by one or more, for example, one, two, three, or four, identical or different substituents. Aryl residues can be bonded via any desired position, and in substituted aryl residues the substituents can be located in any desired position.

In monosubstituted phenyl residues, the substituent can be located in the 2-position, the 3-position, or the 4-position, the 3-position and the 4-position being preferred. If a phenyl group carries two substituents, they can be located in 2,3-position, 2,4-position, 2,5-position, 2,6-position, 3,4-position, or 3,5-position. In phenyl residues carrying three substituents, the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues, the substituents can be located in any positions, for example, in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl, or 4-biphenylyl. Fluorenyl residues can be 1-, 2-, 3-, 4-, or 9-fluorenyl. In monosubstituted fluorenyl residues, bonded via the 9-position the substituent is preferably present in the 1-, 2-, 3-, or 4-position.

Unless stated otherwise, substituents that can be present in substituted aryl groups are, for example, ($C_1$–$C_8$)-alkyl, in particular ($C_1$–$C_4$)-alkyl, such as methyl, ethyl, or tert-butyl, hydroxy, ($C_1$–$C_8$)-alkyloxy, in particular ($C_1$–$C_4$)-alkyloxy, such as methoxy, ethoxy, or tert-butoxy, methylenedioxy, ethylenedioxy, F, Cl, Br, I, cyano, nitro, trifluoromethyl, trifluoromethoxy, hydroxymethyl, formyl, acetyl, amino, mono- or di-($C_1$–$C_4$)-alkylamino, (($C_1$–$C_4$)-alkyl)carbonylamino like acetylamino, hydroxycarbonyl, (($C_1$–$C_4$)-alkyloxy)carbonyl, carbamoyl, optionally substituted phenyl, benzyl optionally substituted in the phenyl group, optionally substituted phenoxy, or benzyloxy optionally substituted in the phenyl group. A substituted aryl group that can be present in a specific position of compounds of formula I can, independently of other aryl groups, be substituted by substituents selected from any desired subgroup of the substituents listed above and/or in the definition of that group. For example, a substituted aryl group may be substituted by one or more identical or different substituents selected from ($C_1$–$C_4$)-alkyl, hydroxy, ($C_1$–$C_4$)-alkyloxy, F, Cl, Br, I, cyano, nitro, trifluoromethyl, amino, phenyl, benzyl, phenoxy, and benzyloxy. Preferably, not more than two nitro groups are present in compounds of formula I.

The above statements relating to aryl groups correspondingly apply to divalent residues derived from aryl groups, i.e., to arylene groups like phenylene which can be unsubstituted or substituted 1,2-phenylene, 1,3-phenylene, or 1,4-phenylene, or naphthalene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl. The above statements also correspondingly apply to the aryl subgroup in arylalkyl- groups. Examples of arylalkyl- groups which can also be unsubstituted or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl. All these explanations also corresponding apply to aromatic rings which may be condensed (or fused) to a ring formed by the groups $R^{21}$ and $R^{22}$ and the carbon atom to which these groups are attached.

The Het group comprises groups containing 3, 4, 5, 6, 7, 8, 9, or 10 ring atoms in the parent monocyclic or bicyclic heterocyclic ring system. In monocyclic Het groups, the heterocyclic ring preferably is a 3-membered, 4-membered, 5-membered, 6-membered, or 7-membered ring, particularly preferably, a 5-membered or 6-membered ring. In bicyclic Het groups, preferably two fused rings are present, one of which is a 5-membered ring or 6-membered heterocyclic ring and the other of which is a 5-membered or 6-membered heterocyclic or carbocyclic ring, i.e., a bicyclic Het ring preferably contains 8, 9, or 10 ring atoms, more preferably 9 or 10 ring atoms.

Het comprises saturated heterocyclic ring systems which do not contain any double bonds within the rings, as well as mono-unsaturated and poly-unsaturated heterocyclic ring systems which contain one or more, for example, one, two, three, four, or five, double bonds within the rings provided that the resulting system is stable. Unsaturated rings may be non-aromatic or aromatic, i.e., double bonds within the rings in the Het group may be arranged in such a manner that a conjugated pi electron system results. Aromatic rings in a Het group may be 5-membered or 6-membered rings, i.e., aromatic groups in a Het group contain 5 to 10 ring atoms. Aromatic rings in a Het group thus comprise 5-membered and 6-membered monocyclic heterocycles and bicyclic heterocycles composed of two 5-membered rings, one 5-membered ring, and one 6-membered ring, or two 6-membered rings. In bicyclic aromatic groups in a Het group, one or both rings may contain heteroatoms. Aromatic Het groups may also be referred to by the customary term heteroaryl for which all the definitions and explanations above and below relating to Het correspondingly apply. All these explanations also corresponding apply to heteroaromatic rings which may be condensed (or fused) to a ring formed by the $R^{21}$ and $R^{22}$ groups and the carbon atom to which these groups are attached.

Unless stated otherwise, in the Het groups and any other heterocyclic groups, preferably 1, 2, 3, or 4 identical or different ring heteroatoms selected from nitrogen, oxygen, and sulfur are present. Particularly preferably, in these groups 1 or 2 identical or different ring heteroatoms selected from nitrogen, oxygen, and sulfur are present. The ring heteroatoms can be present in any desired number and in any position with respect to each other provided that the resulting heterocyclic system is known in the art and is stable and suitable as a subgroup in a drug substance. Examples of parent structures of heterocycles from which the Het group can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, or pteridine, as well as ring systems which result from the listed heterocycles by fusion (or condensation) of a carbocyclic ring, for example, benzo-fused, cyclopenta-fused, cyclohexa-fused, or cyclohepta-fused derivatives of these heterocycles.

The fact that many of the before-listed names of heterocycles are the chemical names of unsaturated or aromatic ring systems does not imply that the Het groups could only be derived from the respective unsaturated ring system. The names here only serve to describe the ring system with respect to ring size and the number of the heteroatoms and their relative positions. As explained above, the Het group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which the Het groups may be derived, the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, or 1,2,3,4-tetrahydroisoquinoline.

The Het residue may be bonded via any ring carbon atom, and in the case of nitrogen heterocycles, via any suitable ring nitrogen atom. Thus, for example, a pyrrolyl residue can be 1-pyrrolyl, 2-pyrrolyl, or 3-pyrrolyl, a pyrrolidinyl residue can be 1-pyrrolidinyl (=pyrrolidino), 2-pyrrolidinyl, or 3-pyrrolidinyl, a pyridyl residue can be 2-pyridyl, 3-pyridyl, or 4-pyridyl, and a piperidinyl residue can be 1-piperidinyl (=piperidino), 2-piperidinyl, 3-piperidinyl, or 4-piperidinyl. Furyl can be 2-furyl or 3-furyl, thienyl can be 2-thienyl or 3-thienyl, imidazolyl can be 1-imidazolyl, 2-imidazolyl, 4-imidazolyl, or 5-imidazolyl, 1,3-oxazolyl can be 1,3-oxazol-2-yl, 1,3-oxazol-4-yl, or 1,3-oxazol-5-yl, 1,3-thiazolyl can be 1,3-thiazol-2-yl, 1,3-thiazol-4-yl, or 1,3-thiazol-5-yl, pyrimidinyl can be 2-pyrimidinyl, 4-pyrimidinyl (=6-pyrimidinyl), or 5-pyrimidinyl, and piperazinyl can be 1-piperazinyl (=4-piperazinyl=piperazino) or 2-piperazinyl. Indolyl can be 1-indolyl, 2-indolyl, 3-indolyl, 4-indolyl, 5-indolyl, 6-indolyl, or 7-indolyl. Similarly, benzimidazolyl, benzoxazolyl, and benzothiazolyl residues can be bonded via the 2-position and via any of the positions 4, 5, 6, and 7, benzimidazolyl also via the 1-position. Quinolyl can be 2-quinolyl, 3-quinolyl, 4-quinolyl, 5-quinolyl, 6-quinolyl, 7-quinolyl, or 8-quinolyl, and isoquinolyl can be 1-isoquinolyl, 3-isoquinolyl, 4-isoquinolyl, 5-isoquinolyl, 6-isoquinolyl, 7-isoquinolyl, or 8-isoquinolyl. In addition to being bonded via any of the positions indicated for quinolyl and isoquinolyl, 1,2,3,4-tetrahydroquinolyl and 1,2,3,4-tetrahydroisoquinolyl can also be bonded via the nitrogen atoms in the 1-position and 2-position, respectively.

Unless stated otherwise, and irrespective of any specific substituents bonded to Het groups or any other heterocyclic groups which are indicated in the definition of compounds of formula I, the Het group can be unsubstituted or substituted on ring carbon atoms with one or more, for example, one, two, three, four, or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl, 1-hydroxyethyl, or 2-hydroxyethyl, methylenedioxy, ethylenedioxy, formyl, acetyl, cyano, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, or benzyloxy optionally substituted in the phenyl group. The substituents can be present in any desired position provided that a stable molecule results. Of course an oxo group cannot be present in an aromatic ring. Each suitable ring nitrogen atom in a Het group can independently of each other be unsubstituted, i.e., carry a hydrogen atom, or can be substituted, i.e., carry a substituent like $(C_1-C_8)$-alkyl, for example, $(C_1-C_4)$-alkyl such as methyl or ethyl, optionally substituted phenyl, phenyl-$(C_1-C_4)$-alkyl, for example, benzyl, optionally substituted in the phenyl group, hydroxy-$(C_2-C_4)$-alkyl such as, for example, 2-hydroxyethyl, acetyl, or another acyl group, methylsulfonyl or another sulfonyl group, aminocarbonyl, or $(C_1-C_4)$-alkyloxycarbonyl. Nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydrothienyl residue or a thiomorpholinyl residue like 4-thiomorpholinyl may be present as 1-oxo4-thiomorpholinyl or 1,1-dioxo-4-thiomorpholinyl. A substituted Het group that can be present in a specific position of compounds of formula I can independently of other Het groups be substituted by substituents selected from any desired subgroup of the substituents listed before and/or in the definition of that group.

The explanations relating to the Het residue correspondingly apply to divalent Het residues including divalent heteroaromatic residues which may be bonded via any two ring carbon atoms and in the case of nitrogen heterocycles via any carbon atom and any suitable ring nitrogen atom or via any two suitable nitrogen atoms. For example, a pyridinediyl residue can be 2,3-pyridinediyl, 2,4-pyridinediyl, 2,5-pyridinediyl, 2,6-pyridinediyl, 3,4-pyridinediyl, or 3,5-pyridinediyl, a piperidinediyl residue can be, among others, 1,2-piperidinediyl, 1,3-piperidinediyl, 1,4-piperidinediyl, 2,3-piperidinediyl, 2,4-piperidinediyl, or 3,5-piperidinediyl, and a piperazinediyl residue can be, among others, 1,3-piperazinediyl, 1,4-piperazinediyl, 2,3-piperazinediyl, or 2,5-piperazinediyl. The above statements also correspondingly apply to the Het subgroup in the Het-alkyl- groups. Examples of such Het-alkyl- groups which can also be unsubstituted or substituted in the Het subgroup as well as in the alkyl subgroup, are (2-pyridyl)methyl, (3-pyridyl)methyl, (4-pyridyl)methyl, 2-(2-pyridyl)ethyl, 2-(3-pyridyl)ethyl, or 2-(4-pyridyl)ethyl.

Halogen is fluorine, chlorine, bromine, or iodine, preferably fluorine, chlorine, or bromine, particularly preferably chlorine or bromine.

Optically active carbon atoms present in compounds of formula I can independently of each other have R configuration or S configuration. Compounds of formula I can be present in the form of pure enantiomers or pure diastereomers or in the form of mixtures of enantiomers and/or diastereomers, for example, in the form of racemates. The present invention relates to pure enantiomers and mixtures of enantiomers as well as to pure diastereomers and mixtures of diastereomers. The invention comprises mixtures of two or more stereoisomers of formula I, and it comprises any ratio of the stereoisomers in the mixtures. Compounds of formula I can be present as E isomers or Z isomers (or cis isomers or trans isomers) and the invention relates both to pure E isomers and pure Z isomers and to E/Z mixtures in any ratio. The invention also comprises all tautomeric forms of compounds of formula I.

Diastereomers, including E/Z isomers, can be separated into the individual isomers, for example, by chromatography. Racemates can be separated into the two enantiomers by customary methods, for example, by chromatography on chiral phases or by resolution, for example, by crystallization of diastereomeric salts obtained with optically active acids or bases. Stereochemically uniform compounds of formula I can also be obtained by employing stereochemically uniform starting materials or by using stereoselective reactions.

The choice of incorporating a building block with R configuration or S configuration into a compound of formula I, or in the case of an amino acid unit present in a compound of formula I, of incorporating a building block designated as D-amino acid or L-amino acid, can depend, for example, on the desired characteristics of the compound of formula I. For example, the incorporation of a D-amino acid building block can confer increased stability in vitro or in vivo. The incorporation of a D-amino acid building block also can achieve a desired increase or decrease in the pharmacological activity of the compound. In some cases, it can be desirable to allow the compound to remain active for only a short period of time. In such cases, the incorporation of an L-amino acid building block in the compound can allow endogenous peptidases in an individual to digest the compound in vivo, thereby limiting the individual's exposure to the active compound. A similar effect may also be observed in compounds of the invention by changing the configuration in another building block from S configuration to R configuration or vice versa. By taking into consideration the medical needs, one skilled in the art can determine the desirable characteristics, for example, a favorable stereochemistry, of the required compound of the invention.

Physiologically tolerable salts of compounds of formula I are nontoxic salts that are physiologically acceptable, in particular pharmaceutically utilizable salts. Such salts of compounds of formula I containing acidic groups, for example, a carboxy COOH group, are, for example, alkali metal salts or alkaline earth metal salts such as sodium salts, potassium salts, magnesium salts, and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine, or tris-(2-hydroxyethyl)amine. Basic groups contained in compounds of formula I, for example, amino groups, amidino groups, or guanidino groups, form acid addition salts, for example, with inorganic acids such as hydrochloric acid, hydrobromic acid, sulfuric acid, nitric acid, or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid, or p-toluenesulfonic acid. Compounds of formula I which simultaneously contain a basic group and an acidic group, for example, an amidino group and a carboxy group, can also be present as zwitterions (betaines) which are likewise included in the present invention.

Salts of compounds of formula I can be obtained by customary methods known to those skilled in the art, for example, by combining a compound of formula I with an inorganic or organic acid or base in a solvent or dispersant, or from other salts by cation exchange or anion exchange. The present invention also includes all salts of compounds of formula I which, because of low physiologically tolerability, are not directly suitable for use in pharmaceuticals but are suitable, for example, as intermediates for carrying out further chemical modifications of compounds of formula I or as starting materials for the preparation of physiologically tolerable salts.

The present invention further includes all solvates of compounds of formula I, for example, hydrates or adducts with alcohols. The invention also includes derivatives and modifications of compounds of formula I, for example, prodrugs, protected forms, and other physiologically tolerable derivatives including esters and amides, as well as active metabolites of compounds of formula I. Such esters and amides are, for example, $(C_1-C_4)$-alkyl esters, unsubstituted amides, or $(C_1-C_4)$-alkylamides. The invention relates in particular to prodrugs and protected forms of compounds of formula I which can be converted into compounds of formula I under physiological conditions. Suitable prodrugs for compounds of formula I, i.e., chemically modified derivatives of compounds of formula I having properties which are improved in a desired manner, for example, with respect to solubility, bioavailability, or duration of action, are known to those skilled in the art. More detailed information relating to prodrugs is found in standard literature like, for example, *Design of Prodrugs*, H. Bundgaard (ed.), Elsevier (1985); Fleisher et al., *Advanced Drug Delivery Reviews* 19 (1996) 115–130; or H. Bundgaard, *Drugs of the Future* 16 (1991) 443, which are all incorporated herein by reference. Suitable prodrugs for compounds of formula I are especially ester prodrugs and amide prodrugs of carboxylic acid groups, and also acyl prodrugs and carbamate prodrugs of acylatable nitrogen-containing groups such as amino groups, amidino groups, and guanidino groups. In the acyl prodrugs and carbamate prodrugs, one or more, for example, one or two, hydrogen atoms on nitrogen atoms in such groups are replaced with an acyl group or a carbamate group. Suitable acyl groups and carbamate groups for acyl prodrugs and carbamate prodrugs are, for example, the $R^{p1}$—CO— and $R^{p2}$O—CO— groups, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, Het-, $(C_6-C_{14})$-aryl-$(C_1-C_4)$-alkyl-, or Het-$(C_1-C_4)$-alkyl-, and in which $R^{p2}$ has the meanings indicated for $R^{p1}$ with the exception of hydrogen.

From another point of view, the concept of converting a compound of formula I into a derivative or a prodrug can also be regarded as protecting or masking functional groups like amino groups, amidino groups, guanidino groups, or carboxy groups that are present in the compound of formula I. As already mentioned, the present invention also relates to all such protected forms for which some details are exemplarily given in the following.

For example, compounds of the invention can be chemically modified or protected at any amino group such that the amino group carries as a substituent, for example, an acetyl, cyclopentylcarbonyl, allyloxycarbonyl, propyloxycarbonyl, benzoyl, or other such group, in which groups further substituents can optionally be present as described above. The term amino group is used broadly herein to refer to any acylatable amino group, including a primary or secondary amino group. Such amino groups can occur, for example, at the N-terminus of the compound of formula I, or as substituents in alkyl groups or aryl groups or in the side chain of an amino acid building block, for example, in the groups $R^{96}$, $R^{97}$, or $R^2$. The term N-terminus refers to the α-amino group of the first amino acid unit present in a compound of formula I written in the conventional manner of representing a peptide, i.e., to the $R^1(R^{91})N$ group. Specifically, the N-terminus of a compound of the invention can be protected by linking thereto an amino-protecting group.

The term protecting group (or blocking group) is used broadly herein to refer to a conventional chemical group that can replace a hydrogen atom present in an amino group and that is introduced by reacting the amino group with an amino-protecting agent, including, for example, the α-amino group present at the N-terminus of a compound of the invention. An amino-protecting group protects the otherwise reactive amino group against undesirable reactions as can occur, for example, due to exopeptidase activity on a final compound of formula I but also, for example, during a synthetic procedure or during storage of a compound. As already mentioned, the modification of an amino group can also provide additional advantages including, for example, increasing the solubility or the bioactivity of the compound. Various amino-protecting groups are known in the art and include, for example, acyl groups such as formyl, acetyl, picoloyl, tert-butylacetyl, tert-butyloxycarbonyl, allyloxycarbonyl, benzyloxycarbonyl, or benzoyl groups, as well as aminoacyl residues which themselves can be modified by an amino-protecting group. Other amino-protecting groups are described, for example, in Gross and Meienhofer (eds.), *The Peptides*, vol. 3, Academic Press (1981), or in Greene and Wuts, *Protective Groups in Organic Synthesis*, 2nd ed., 309–405, John Wiley & Sons (1991), each of which is incorporated herein by reference. The product of any such modification of the N-terminus amino group of a compound of formula I is referred to as an N-terminal derivative.

The above explanations relating to protecting groups on amino groups in compounds of formula I correspondingly apply to protecting groups on amidino groups and guanidino groups. Like in an amino group, in these latter groups which may, for example, represent the $R^{95}$ residue, a hydrogen atom may be replaced with an acyl group like, for example, formyl, $((C_1-C_4)$-alkyl)carbonyl, $((C_1-C_4)$-alkyl)oxycarbonyl, $(C_6-C_{14})$-arylcarbonyl, or $(C_6-C_{14})$-aryl-$(C_1-C_4)$-alkyloxycarbonyl in order to improve the property profile of a compound of formula I in a desired manner.

Similarly, compounds of the invention can be chemically modified at any carboxy group by introducing a carboxy-protecting group. The term protecting group (or blocking group) is also used broadly herein to refer to a conventional chemical group that can replace the hydrogen atom or the hydroxy group or the oxo group of a carboxy group (COOH) or the total carboxy group. Carboxy groups that may advantageously be present in protected form or modified form can occur, for example, as substituents in alkyl groups or aryl group or in the side chain of an amino acid building block, for example, in the groups $R^{96}$, $R^{97}$, and $R^2$. A carboxy group can be protected or modified, for example, by a conventional reduction of the carboxy group or of a derivative thereof like an ester which leads to an alcohol $CH_2OH$ group or an aldehyde CHO group that replaces the COOH group. A carboxy group can also be protected by converting the COOH group into an ester group, for example, by formation of an oral ester. Oral esters are well known in the art and include, for example, alkyloxymethyl esters such as $(C_1-C_4)$-alkyloxymethyl esters like methoxymethyl, ethoxymethyl, isopropoxymethyl esters, and the like; 1-$(C_1-C_4)$-alkyloxyethyl esters such as 1-methoxyethyl, 1-ethoxyethyl, 1-propoxyethyl, 1-isopropoxyethyl esters, and the like; 2-oxo-1,3-dioxolen-4-ylmethyl esters such as 5-methyl-2-oxo-1,3-dioxolen-4-ylmethyl, 5-phenyl-2-oxo-1,3-dioxolen4-ylmethyl esters, and the like; $(C_1-C_4)$-alkylthiomethyl esters such as methylthiomethyl, ethylthiomethyl, isopropylthiomethyl esters, and the like; acyloxymethyl esters such as pivaloyloxymethyl, acetoxymethyl esters, and the like; 1-ethoxycarbonylmethyl ester; 1-acyloxy-1-substituted methyl esters such as 1-acetoxyethyl; 3-phthalidyl or 5,6-dimethyl-3-phthalidyl esters; 1-$((C_1-C_4)$-alkyloxycarbonyloxy)ethyl esters such as 1-(ethoxycarbonyloxy)ethyl ester; and 1-$((C_1-C_4)$-alkylaminocarbonyloxy)ethyl esters such as 1-(methylaminocarbonyloxy)ethyl ester. A carboxy group may also be modified by replacement of the total carboxy group with a substituent such as a 2-thiazolyl, tetrazolyl, cyclohexyl, or another group. Carboxy-protecting groups like the above ones are well known in the art (see, for example, Greene and Wuts, loc. cit., 224–276) and protect a carboxy group against undesirable reactions as explained above with respect to amino-protecting groups.

The —N($R^{92}$)—C($R^{96}$)($R^{97}$)—CO— unit present in compounds of formula I represents the residue of an α-amino acid which is formally obtained from the respective α-amino acid by removing a hydrogen atom from the N-terminal amino group and the hydroxy group from the C-terminal carboxy group as is customary in peptide chemistry. The $R^{96}$ and/or $R^{97}$ groups may thus be regarded as corresponding to the groups bonded to the central carbon atom of an α-amino acid, i.e., in the case of an α-monosubstituted α-aminoacid the $R^{96}$ group corresponds to the hydrogen atom attached to the central carbon atom and the $R^{97}$ group corresponds to the side chain of the amino acid. As is outlined below, the —N($R^{92}$)—C($R^{96}$)($R^{97}$)—CO— unit may be synthetically incorporated into compounds of formula I by employing as a building block the respective amino acid of formula HN($R^{92}$)—C($R^{96}$)($R^{97}$)—COOH. Parent amino acids from which the —N($R^{92}$)—C($R^{96}$)($R^{97}$)—CO— unit may be derived can be natural or unnatural amino acids, examples of which are Aad, Asn, Asp, Gln, Glu, hGln, or hGlu. Functional groups in such amino acids can be present in protected form or can be derivatized. Similarly, the —N($R^{91}$)—CH(—($CH_2$)-(substituted phenyl))—CO— unit present in compounds of formula I represents the residue of an α-amino acid.

Besides compounds of formula I which are defined as described at the beginning, a second subject of the present invention are also compounds of formula I in which all residues, groups, and numbers are defined as described at the beginning except for the $R^{98}$ and $R^{99}$ residues which in this second embodiment of the invention are independent of each other and can be identical or different and are selected from hydrogen, hydroxycarbonyl-, ($C_1$–$C_8$)-alkyloxycarbonyl-, ($C_6$–$C_{14}$)-aryloxycarbonyl-, ($C_6$–$C_{14}$)-aryl-($C_1$–$C_4$)-alkyloxycarbonyl-, aminocarbonyl-, ($C_1$–$C_8$)-alkylaminocarbonyl-, tetrazolyl, —P(O)(OH)$_2$, —S(O)$_2$OH, and —S(O)$_2$NH$_2$, in any stereoisomeric form or mixture thereof in any ratio, or a physiologically tolerable salt thereof, with the proviso that in this second embodiment of the invention the compounds acetyl-(4-amidinophenylalanyl)-cyclohexylglycyl-(4-methylpyridiniummethyl)amide, acetyl-(4-amidinophenylalanyl)-cyclohexylglycyl-(2-(3-methylpyridinium)ethyl)amide, acetyl-(4-amidinophenylalanyl)-cyclohexylglycyl-(2-(4-methylpyridinium)ethyl)amide, acetyl-(4-amidinophenylalanyl)-cyclohexylglycyl-(4-amidinobenzyl)amide, acetyl-(4-amidinophenylalanyl)-cyclohexylglycyl-(3-amidinobenzyl)amide, and acetyl-(4-amidinophenylalanyl)-cyclohexyl lycyl-(1-(4-methylpyridinium)ethyl)amide are excluded. For this second embodiment of the invention, the explanations above and below, for example, those relating to alkyl groups, aryl groups, or heterocyclic groups, or to salts or stereoisomeric forms of the compounds, as well as those relating to preferred denotations, correspondingly apply. In this second embodiment of the invention, a further preferred denotation of $R^{98}$ and $R^{99}$, independently of each other, is hydrogen. There may be mentioned as examples of parent amino acids, from which in this second embodiment of the invention the —N($R^{92}$)—C($R^{96}$)($R^{97}$)—CO— unit may be derived, Aad, Ala, Asn, Asp, Gln, Glu, hAla, hGln, hGlu, His, hule, hLeu, hPhe, hTrp, hTyr, Ile, Leu, Nle, Nva, Phe, Phg, Thi, Trp, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, or 2-(p-chlorophenyl)aminoacetic acid (cf. Houben-Weyl, *Methoden der Organischen Chemie* (Methods of Organic Chemistry), Vol. 15/1 and 15/2, Georg Thieme Verlag, Stuttgart (1974)), where functional groups in these amino acids can be present in protected form or can be derivatized.

The structural elements in compounds of formula I have the following preferred denotations which they can have independently of the denotations of other elements.

The number r, i.e., the number of $CH_2$ groups in the polymethylene chain connecting the phenyl group depicted in formula I and the carbon atom which carries the amino $R^1(R^{91})N$ group, preferably is 0, 1, or 2, more preferably 0 or 1, particularly preferably 1. Thus, preferably the —($CH_2$)$_r$— group is a direct bond or one of the —$CH_2$— or —$CH_2$—$CH_2$— groups, more preferably a direct bond or the —$CH_2$— group, particularly preferably the —$CH_2$— group.

The number s, i.e., the number of $R^{94}$ substituents present on the phenyl group depicted in formula I, preferably is 0, 1, or 2, more preferably 0 or 1, particularly preferably 0. If all $R^{94}$ substituents present on the phenyl group are halogen atoms, in particular fluorine atoms, a further preferred denotation of s is 4. Positions on the phenyl group to which neither a $R^{94}$ substituent nor the $R^{95}$—($CH_2$)$_t$— group are bonded carry hydrogen atoms. If, for example, s is 0, the phenyl group carries the $R^{95}$—($CH_2$)$_t$— group which at any rate is present in compounds of formula I, and four hydrogen atoms. The $R^{95}$—($CH_2$)$_t$— group can be present in any desired position of the phenyl ring, i.e., in the 2-position, the 3-position, or the 4-position. Preferably, the $R^{95}$—($CH_2$)$_t$— group is present in the 3-position or the 4-position, more preferably it is present in the 4-position (with respect to the ($CH_2$)$_r$ group). $R^{94}$ substituents can be present in any desired position of the phenyl group not occupied by the $R^{95}$—($CH_2$)$_t$— group. Thus, if the $R^{95}$—($CH_2$)$_t$— group is present in the 4-position and s is 1, the single $R^{94}$ substituent can be present in the 2-position or the 3-position where the 3-position is preferred. If the $R^{95}$—($CH_2$)$_t$— group is present in the 3-position (with respect to the ($CH_2$)$_r$ group) and s is 1, the single $R^{94}$ substituent can be present in the 2-position, the 4-position, the 5-position, or the 6-position where the 4-position is preferred. If the $R^{95}$—($CH_2$)$_t$— group is present in the 4-position and s is 2, the two $R^{94}$ substituents can be present in the 2,3-position, 2,5-position, 2,6-position, or the 3,5-position where the 3,5-position is preferred.

The number t, i.e., the number of $CH_2$ groups in the polymethylene chain connecting the phenyl group depicted in formula I and the $R^{95}$ group, preferably is 0 or 1, more preferably 0. Thus, preferably, the —($CH_2$)$_t$— group is a direct bond or the —$CH_2$— group. More preferably, the —($CH_2$)$_t$— group is a direct bond, i.e., the $R^{95}$ group is directly bonded to the phenyl group.

$R^1$ preferably is $R^{11}$—CO— or $R^{12}$—$SO_2$—, more preferably $R^{11}$—CO—.

$R^{11}$ preferably is ($C_1$–$C_8$)-alkyl, ($C_6$–$C_{14}$)-aryl, ($C_6$–$C_{14}$)-aryl-($C_1$–$C_4$)-alkyl-, ($C_1$–$C_8$)-alkyloxy-, or ($C_6$–$C_{14}$)-aryl-($C_1$–$C_4$)-alkyloxy-, where all these groups can be unsubstituted or substituted by one or more identical or different $R^{40}$ substituents. More preferably, $R^{11}$ is ($C_1$–$C_8$)-alkyl, ($C_6$–$C_{14}$)-aryl, or ($C_1$–$C_8$)-alkyloxy-, particularly preferably ($C_6$–$C_{14}$)-aryl or ($C_1$–$C_8$)-alkyloxy-, where all these groups can be unsubstituted or substituted by one or more identical or different $R^{40}$ substituents. A ($C_1$–$C_8$)-alkyl group representing $R^{11}$, or present in a group representing $R^{11}$, preferably is a ($C_2$–$C_8$)-alkyl group, more preferably a ($C_2$–$C_6$)-alkyl group, for example, an allyl group or a cyclopropylmethyl- group. A $(C_6-C_{14})$-aryl group representing $R^{11}$ or present in a group representing $R^{11}$ preferably is a $(C_6-C_{10})$-aryl group, more preferably a phenyl group. Thus, among particularly preferred groups representing $R^{11}$ are, for example, $(C_2-C_6)$-alkyloxy- and phenyl which groups can be unsubstituted or substituted by one or more identical or different $R^{40}$ substituents.

As explained above with respect to alkyl groups in general, an alkyl group representing $R^{11}$ or present in a group representing $R^{11}$ can be saturated or unsaturated and can be acyclic or cyclic. Preferably, an alkyl group representing $R^{11}$ or present in a group representing $R^{11}$ is an unsaturated acyclic alkyl group or a saturated alkyl group containing a cyclic group like a cycloalkyl group or a cycloalkyl-alkyl- group. More preferably, such an alkyl group is an unsaturated acyclic alkyl group, for example, an alkyl group containing one or two double bonds and/or triple bonds, preferably one or two double bonds or one triple bond, particularly preferably one double bond, or a cycloalkyl-alkyl- group. Particularly preferably such an alkyl group is an unsaturated acyclic alkyl group. Examples of such preferred alkyl groups representing $R^{11}$ or present, for example, in an alkyloxy- group representing $R^{11}$ are ethenyl (=vinyl) $CH_2=CH-$, 1-propenyl $CH_3-CH=CH-$, 2-propenyl (=allyl) $CH_2=CH-CH_2-$, E- and Z-2-butenyl $CH_3-CH=CH-CH_2-$, 3-methyl-2-butenyl $(CH_3)_2C=CH-CH_2-$, 1,3-pentadienyl $CH_3-CH=CH-CH=CH-$, cyclopropyl, cyclopropyl-methyl-, 2-cyclopropyl-ethyl-, cyclopentyl, cyclopentyl-methyl-, cyclohexyl, or cyclohexyl-methyl-. Thus, in a preferred embodiment of the present invention, $R^{11}$ is unsaturated $(C_2-C_8)$-alkyloxy-, in particular unsaturated $(C_2-C_6)$-alkyloxy-, especially unsaturated $(C_3-C_6)$-alkyloxy-, containing one or two double bonds, in particular one double bond, or is saturated $(C_3-C_6)$-cycloalkyl-$(C_1-C_2)$-alkyloxy-, in particular saturated $(C_3-C_6)$-cycloalkyl-methyloxy-, especially cyclopropyl-methyloxy-, or is phenyl, where the alkyloxy-, cycloalkyl-alkyloxy-, and phenyl groups can be unsubstituted or substituted by one or more identical or different $R^{40}$ substituents. In a more preferred embodiment of the present invention, $R^{11}$ is unsaturated $(C_2-C_6)$-alkyloxy- containing one double bond, in particular unsaturated $(C_3-C_6)$-alkyloxy-, especially allyloxy-, or cyclopropyl-methyloxy-, where the alkyloxy-, the allyloxy-, and cyclopropyl-methyloxy- groups can be unsubstituted or substituted by one or more identical or different $R^{40}$ substituents. In an especially preferred embodiment of the present invention, $R^{11}$ is unsaturated $(C_2-C_6)$-alkyloxy- containing one double bond, in particular unsaturated $(C_3-C_6)$-alkyloxy-, especially allyloxy-, where the alkyloxy- and the allyloxy- groups can be unsubstituted or substituted by one or more identical or different $R^{40}$ substituents.

If a $R^{11}$ group is substituted by one or more $R^{40}$ substituents, it preferably is substituted by one, two, or three identical or different $R^{40}$ substituents, particularly preferably by one or two $R^{40}$ substituents. $R^{40}$ substituents present on the $R^{11}$ group preferably are identical or different groups selected from halogen, $(C_1-C_4)$-alkyl, and trifluoromethyl wherein halogen, preferably, is fluorine, chlorine, or bromine, in particular bromine or chlorine. $R^{40}$ substituents can be present in any desired position of the $R^{11}$ group.

$R^{12}$ preferably is $(C_1-C_8)$-alkyl, $(C_6-C_{14})$-aryl, particularly preferably $(C_1-C_8)$-alkyl or $(C_6-C_{10})$-aryl, where all these groups can be unsubstituted or substituted by one or more identical or different $R^{40}$ substituents. If a $R^{12}$ group is substituted by one or more $R^{40}$ substituents it preferably is substituted by one, two, or three identical or different $R^{40}$ substituents, particularly preferably by one or two $R^{40}$ substituents. $R^{40}$ substituents present on the $R^{12}$ group preferably are identical or different groups selected from halogen, $(C_1-C_4)$-alkyl, acetylamino, nitro, and trifluoromethyl wherein halogen preferably is fluorine, chlorine, or bromine, in particular bromine or chlorine. $R^{40}$ substituents can be present in any desired position of the $R^{12}$ group.

$R^2$ preferably is $R^{21}(R^{22})CH-$, $R^{23}-\text{Het-}(CH_2)_k-$, $R^{23}(R^{24})N-(CH_2)_m-D-(CH_2)_n-$, or $R^{25}(R^{26})N-CO-(CH_2)_p-D-(CH_2)_q-$, particularly preferably $R^{21}(R^{22})CH-$, $R^{23}-\text{Het-}(CH_2)_k-$, or $R^{23}(R^{24})N-(CH_2)_m-D-(CH_2)_n-$.

A Het group which is present in the $R^{23}-\text{Het-}(CH_2)_k-$ group preferably is a 5- or 6-membered monocyclic or 9- or 10-membered bicyclic saturated or aromatic heterocyclic group containing 1 or 2, in particular 1, identical or different heteroatoms which are selected from nitrogen, oxygen, and sulfur and which preferably are nitrogen atoms. More preferably, such a Het group is a 5- or 6-membered monocyclic saturated or aromatic heterocyclic group. The Het group in the $R^{23}-\text{Het-}(CH_2)_k-$ group can be bonded to the $-(CH_2)_k-$ group via a carbon atom or a suitable nitrogen atom. Preferably, it is bonded via a carbon atom. The Het group in the $R^{23}-\text{Het-}(CH_2)_k-$ group can be unsubstituted, i.e., carry only the $R^{23}$ group and no further substituents, or it can be substituted, i.e., carry further substituents in addition to $R^{23}$ as described above with respect to heterocyclic groups in general. If a Het group carries further substituents in addition to $R^{23}$ it preferably carries one, two, or three identical or different substituents selected from $(C_1-C_4)$-alkyl, $(C_1-C_4)$-alkyloxy, halogen, amino, $(C_1-C_4)$-alkylamino-, di-$((C_1-C_4)$-alkyl)-amino, trifluoromethyl, hydroxy, and oxo.

The $R^{23}$ group present in the $R^{23}-\text{Het-}(CH_2)_k-$ group can be bonded to any desired and suitable position in the Het group. If the $R^{23}$ group in the $R^{23}-\text{Het-}(CH_2)_k-$ group is $R^{27}-SO_2-$ or $R^{28}-CO-$, the Het group preferably is a partially unsaturated or saturated group, in particular a saturated group, and contains a ring nitrogen atom which is not bonded to the $(CH_2)_k$ group and to which ring nitrogen atom the $R^{23}$ group is bonded. If $R^{23}$ in the $R^{23}-\text{Het-}(CH_2)_k-$ group is $R^{27}-SO_2-$ or $R^{28}-CO-$, the Het group in the $R^{23}-\text{Het-}(CH_2)_k-$ group particularly preferably is a saturated 5-membered or 6-membered ring which contains one nitrogen atom as a ring heteroatom, i.e., a pyrrolidine or a piperidine group, and which is bonded to the $(CH_2)_k$ group via the 3-position in the case of a pyrrolidine group or via the 3-position or the 4-position, in particular via the 4-position, in the case of a piperidine group, and the nitrogen atom of which carries the $R^{23}$ group. If the Het group in the $R^{23}-\text{Het-}(CH_2)_k-$ group is an aromatic heterocyclic group the $R^{23}$ group in the $R^{23}-\text{Het-}(CH_2)_k-$ group preferably is hydrogen.

D preferably is a divalent $-C(R^{31})(R^{32})-$ residue, a divalent $(C_6-C_{10})$-arylene residue, or a divalent residue derived from an aromatic monocyclic or bicyclic Het group containing 5 to 10 ring atoms of which 1 or 2 are identical or different ring heteroatoms selected from nitrogen, oxygen, and sulfur. D more preferably is a divalent $-C(R^{31})(R^{32})-$ residue, a divalent phenylene residue, in particular 1,3-phenylene or 1,4-phenylene, or a divalent residue derived from an aromatic monocyclic Het group containing 5 or 6 ring atoms of which 1 or 2 are identical or different ring heteroatoms selected from nitrogen, oxygen, and sulfur. D particularly preferably is a divalent $-C(R^{31})(R^{32})-$ residue or a divalent phenylene residue. In an aromatic Het group representing D, preferably 1 or 2 nitrogen atoms are present as ring heteroatoms. Arylene groups and Het groups representing D can be substituted as described above with respect to such groups in general.

The numbers k, m, n, p, and q preferably are independently of each other 0, 1, 2, or 3, more preferably 0, 1, or 2, particularly preferably 0 or 1, with the proviso that when D is —C($R^{31}$)($R^{32}$)—, the sum m+n cannot be 0 and the sum p+q cannot be 0. The number k especially preferably is 0. In compounds of formula I in which D is —C($R^{31}$)($R^{32}$)— and both $R^{31}$ and $R^{32}$ are hydrogen, the sum m+n preferably is 2.

A ($C_1$–$C_{12}$)-alkyl group representing the $R^{21}$ or $R^{22}$ groups preferably is an acyclic ($C_1$–$C_8$)-alkyl group, a ($C_3$–$C_8$)-cycloalkyl group, or a ($C_3$–$C_8$)-cycloalkyl-($C_1$–$C_4$)-alkyl- group wherein the ($C_1$–$C_4$)-alkyl group is acyclic. $R^{21}$ and $R^{22}$ preferably independently of each other are hydrogen, acyclic ($C_1$–$C_8$)-alkyl, ($C_3$–$C_8$)-cycloalkyl, ($C_3$–$C_8$)-cycloalkyl-($C_1$–$C_4$)-alkyl-, ($C_6$–$C_{10}$)-aryl, ($C_6$–$C_{10}$)-aryl-($C_1$–$C_4$)-alkyl-, Het-, or Het-($C_1$–$C_4$)-alkyl-, where all these groups are unsubstituted or substituted as indicated above, and wherein a ($C_1$–$C_4$)-alkyl group is acyclic, or $R^{21}$ and $R^{22}$ together with the carbon atom to which they are bonded form a ring as indicated above. More preferably, one of the $R^{21}$ and $R^{22}$ groups is hydrogen or ($C_1$–$C_4$)-alkyl and the other of the $R^{21}$ and $R^{22}$ groups is hydrogen, acyclic ($C_1$–$C_8$)-alkyl, ($C_3$–$C_8$)-cycloalkyl, ($C_3$–$C_8$)-cycloalkyl-($C_1$–$C_4$)-alkyl-, ($C_6$–$C_{10}$)-aryl, ($C_6$–$C_{10}$)-aryl-($C_1$–$C_4$)-alkyl-, Het, or Het-($C_1$–$C_4$)-alkyl-, where all these groups are unsubstituted or substituted as indicated above, and wherein a ($C_1$–$C_4$)-alkyl group is acyclic, or $R^{21}$ and $R^{22}$ together with the carbon atom to which they are bonded form a ring as indicated above. Particularly preferably, one of the $R^{21}$ and $R^{22}$ groups is hydrogen or acyclic ($C_1$–$C_4$)-alkyl and the other of the $R^{21}$ and $R^{22}$ groups is hydrogen, acyclic ($C_1$–$C_4$)-alkyl, ($C_3$–$C_7$)-cycloalkyl, ($C_6$–$C_{10}$)-aryl, or Het-, where all these groups are unsubstituted or substituted as indicated above, or $R^{21}$ and $R^{22}$ together with the carbon atom to which they are bonded form a ring as indicated above.

A Het group present in $R^{21}$ or $R^{22}$ preferably is a monocyclic or bicyclic saturated or aromatic heterocyclic group containing 5 to 10 ring atoms, preferably a monocyclic saturated or aromatic group containing 5 or 6 ring atoms, of which 1 or 2, preferably 1, are heteroatoms selected from nitrogen, oxygen, and sulfur and preferably are nitrogen. A $R^{21}$ or $R^{22}$ group which is substituted by one or more substituents preferably is substituted by 1, 2, or 3 identical or different substituents. Substituents present in $R^{21}$ or $R^{22}$ preferably are selected from halogen, hydroxy, ($C_1$–$C_4$)-alkyloxy-, ($C_1$–$C_4$)-alkyl, ($C_1$–$C_4$)-alkylsulfonyl-, trifluoromethyl, acetylamino-, amino, amidino, guanidino, oxo, nitro, cyano, ($C_1$–$C_4$)-alkylamino-, di-(($C_1$–$C_4$)-alkyl)-amino-, aminocarbonyl-, and aminocarbonyl-($C_1$–$C_4$)-alkyl-.

The saturated or unsaturated carbocyclic ring that may be formed by $R^{21}$ and $R^{22}$, together with the carbon atom to which they are bonded can contain 3, 4, 5, 6, 7, or 8 ring atoms. Preferably, such a ring is a saturated or unsaturated cyclopentane ring or cyclohexane ring. To one or two bonds in a ring formed by $R^{21}$ and $R^{22}$ together with the carbon atom to which they are bonded, identical or different aromatic rings may be condensed (or fused) which are preferably selected from benzene, naphthalene, 5- or 6-membered monocyclic heteroaromatic rings, and 9- or 10-membered bicyclic heteroaromatic rings, where the heteroaromatic rings preferably contain 1 or 2 identical or different heteroatoms selected from nitrogen, oxygen, and sulfur. More preferably, aromatic rings condensed to a carbon carbon bond in a ring formed by $R^{21}$ and $R^{22}$ together with the carbon atom to which they are bonded, are selected from benzene and 5- or 6-membered monocyclic heteroaromatic rings containing 1 or 2 identical or different heteroatoms, in particular 1 heteroatom, selected from nitrogen, oxygen, and sulfur. A particularly preferred aromatic ring that may be condensed to a bond in a ring formed by $R^{21}$ and $R^{22}$ together with the carbon atom to which they are bonded, is the benzene ring.

The resulting $R^{21}$($R^{22}$)CH— group in which $R^{21}$ and $R^{22}$ together with the carbon atom to which they are bonded form a ring and which optionally contains condensed aromatic rings, can be unsubstituted or substituted in any desired position in the ring formed by $R^{21}$ and $R^{22}$ together with the carbon atom to which they are bonded and/or in the optionally condensed aromatic rings. If the resulting cyclic $R^{21}$($R^{22}$)CH— group is substituted, it is preferably substituted by one or more, for example, one, two, or three, identical or different substituents as indicated above. Preferably, substituents present in the resulting cyclic $R^{21}$($R^{22}$)CH— group are selected from halogen, hydroxy, ($C_1$–$C_4$)-alkyloxy-, ($C_1$–$C_4$)-alkyl, ($C_1$–$C_4$)-alkylsulfonyl-, trifluoromethyl, acetylamino-, amino, amidino, guanidino, oxo, nitro, cyano, ($C_1$–$C_4$)-alkylamino-, di-(($C_1$–$C_4$)-alkyl)-amino-, aminocarbonyl-, and aminocarbonyl-($C_1$–$C_4$)-alkyl-, in particular from acetylamino-, amino, ($C_1$–$C_4$)-alkylamino-, and di-(($C_1$–$C_4$)-alkyl)-amino-.

$R^{24}$ preferably is hydrogen, ($C_1$–$C_8$)-alkyl, or ($C_6$–$C_{14}$)-aryl-($C_1$–$C_4$)-alkyl-, more preferably hydrogen, ($C_1$–$C_4$)-alkyl, or phenyl-($C_1$–$C_4$)-alkyl-, particularly hydrogen or ($C_1$–$C_4$)-alkyl, wherein the alkyl groups preferably are acyclic. Especially preferably, $R^{24}$ is hydrogen.

$R^{25}$ and $R^{26}$ preferably are independently of each other hydrogen, ($C_1$–$C_8$)-alkyl, or ($C_6$–$C_{14}$)-aryl-($C_1$–$C_4$)-alkyl-, more preferably hydrogen, ($C_1$–$C_4$)-alkyl, or phenyl-($C_1$–$C_4$)-alkyl-, particularly preferably hydrogen or ($C_1$–$C_4$)-alkyl, where all these groups are unsubstituted or substituted by one or more, for example, one, two, or three, identical or different $R^{40}$ substituents, and wherein the alkyl groups preferably are acyclic. Especially preferably, one of the two $R^{25}$ and $R^{26}$ groups is hydrogen and the other is hydrogen or is different from hydrogen. Most preferably, both $R^{25}$ and $R^{26}$ groups are hydrogen.

$R^{27}$ preferably is ($C_1$–$C_8$)-alkyl, ($C_6$–$C_{14}$)-aryl, ($C_6$–$C_{14}$)-aryl-($C_1$–$C_4$)-alkyl-, Het-, or di-(($C_1$–$C_8$)-alkyl)amino-, more preferably ($C_1$–$C_4$)-alkyl, ($C_6$–$C_{lo}$)-aryl, Het-, or di-(($C_1$–$C_4$)-alkyl)amino-, particularly preferably ($C_1$–$C_4$)-alkyl or ($C_6$–$C_{10}$)-aryl, especially preferably ($C_6$–$C_{10}$)-aryl, where all these groups are unsubstituted or substituted by one or more identical or different $R^{40}$ substituents, and wherein the alkyl groups preferably are acyclic. A Het group representing $R^{27}$ preferably is a monocyclic or bicyclic aromatic heterocyclic group containing 5 to 10 ring atoms, preferably a monocyclic group containing 5 or 6 ring atoms, of which 1 or 2 are heteroatoms selected from nitrogen, oxygen, and sulfur, preferably from nitrogen and sulfur. A $R^{27}$ group which is substituted by $R^{40}$ substituents preferably is substituted by 1, 2, or 3, in particular 1 or 2, identical or different $R^{40}$ substituents. $R^{40}$ substituents present in a $R^{27}$ group preferably are selected from halogen, in particular bromine, chlorine, and fluorine, ($C_1$–$C_4$)-alkyloxy-, ($C_1$–$C_4$)-alkyl, trifluoromethyl, acetylamino-, nitro, and cyano.

$R^{28}$ preferably is ($C_1$–$C_8$)-alkyl, ($C_6$–$C_{14}$)-aryl, ($C_6$–$C_{14}$)-aryl-($C_1$–$C_4$)-alkyl-, Het-, ($C_1$–$C_8$)-alkyloxy-, or ($C_6$–$C_{14}$)- aryl-$(C_1–C_4)$-alkyloxy-, more preferably $(C_1–C_4)$-alkyl, $(C_6–C_{10})$-aryl, Het-, $(C_1–C_4)$-alkyloxy-, or $(C_6–C_{10})$-aryl-$(C_1–C_4)$-alkyloxy-, particularly preferably $(C_1–C_4)$-alkyl, $(C_6–C_{10})$-aryl, $(C_1–C_4)$-alkyloxy-, or $(C_6–C_{10})$-aryl-$(C_1–C_4)$-alkyloxy-, especially preferably $(C_1–C_4)$-alkyl, $(C_1–C_4)$-alkyloxy-, or phenyl-$(C_1–C_4)$-alkyloxy-, where all these groups are unsubstituted or substituted by one or more identical or different $R^{40}$ substituents, and wherein the alkyl groups preferably are acyclic. A Het group representing $R^{28}$ preferably is a monocyclic or bicyclic aromatic heterocyclic group containing 5 to 10 ring atoms, and more preferably a monocyclic group containing 5 or 6 ring atoms, of which 1 or 2 are heteroatoms selected from nitrogen, oxygen, and sulfur. A $R^{28}$ group, which is substituted by $R^{40}$ substituents, preferably is substituted by 1, 2, or 3, in particular 1 or 2, identical or different $R^{40}$ substituents. $R^{40}$ substituents present in a $R^{28}$ group preferably are selected from halogen, in particular bromine, chlorine, and fluorine, $(C_1–C_4)$-alkyloxy-, $(C_1–C_4)$-alkyl, trifluoromethyl, acetylamino-, nitro, and cyano.

A $(C_1–C_{12})$-alkyl group representing the $R^{31}$ or $R^{32}$ groups preferably is an acyclic $(C_1–C_8)$-alkyl group, a $(C_3–C_8)$-cycloalkyl group, or a $(C_3–C_8)$-cycloalkyl-$(C_1–C_4)$-alkyl- group wherein the $(C_1–C_4)$-alkyl group is acyclic. $R^{31}$ and $R^{32}$ preferably are independently of each other hydrogen, acyclic $(C_1–C_8)$-alkyl, $(C_6–C_{14})$-aryl-$(C_1–C_4)$-alkyl-, $(C_3–C_8)$-cycloalkyl-$(C_1–C_4)$-alkyl-, and Het-$(C_1–C_4)$-alkyl- where all these groups are unsubstituted or substituted by one or more, for example, one, two, or three, identical or different $R^{40}$ substituents, and where $(C_1–C_4)$-alkyl groups are acyclic. Preferably, one of the two $R^{31}$ and $R^{32}$ groups is hydrogen and the other is hydrogen or different from hydrogen. An acyclic $(C_1–C_8)$-alkyl present in a $R^{31}$ or $R^{32}$ group preferably is an acyclic $(C_1–C_4)$-alkyl group, and a $(C_6–C_{14})$-aryl present in a $R^{31}$ or $R^{32}$ group preferably is a $(C_6–C_{10})$-aryl group, more preferably a phenyl group, where all these groups are unsubstituted or substituted by one or more identical or different $R^{40}$ substituents. A Het group present in a $R^{31}$ or $R^{32}$ group preferably is a monocyclic or bicyclic saturated or aromatic heterocyclic group containing one or two identical or different ring heteroatoms selected from nitrogen, oxygen, and sulfur, in particular containing one or two nitrogen atoms as ring heteroatoms. $R^{40}$ substituents present in a $R^{31}$ or $R^{32}$ group preferably are selected from halogen, in particular bromine, chlorine, and fluorine, $(C_1–C_4)$-alkyloxy-, $(C_1–C_4)$-alkyl, and trifluoromethyl.

$R^{91}$, $R^{92}$, and $R^{93}$ preferably are independently of each other hydrogen or $(C_1–C_4)$-alkyl, more preferably independently of each other hydrogen or methyl, particularly preferably hydrogen.

$R^{94}$ is preferably selected from $(C_1–C_4)$-alkyl and halogen, where the $R^{94}$ groups are independent of each other and can be identical or different. More preferably, the $R^{94}$ substituents are identical or different halogen atoms. Halogen atoms representing $R^{94}$ groups preferably are chlorine and/or fluorine.

$R^{95}$ preferably is amidino or a derivative thereof like $((C_1–C_4)$-alkyl)oxycarbonylamidino, hydroxyamidino-, or another protected form or derivatized form of an amidino group as described above. More preferably, $R^{95}$ is amidino, $((C_1–C_4)$-alkyl)oxycarbonylamidino, or hydroxyamidino-. Particularly preferably, $R^{95}$ is amidino, i.e., the $H_2N$—C(=NH)— group also designated as amino-imino-methyl-group or carbamimidoyl group.

$R^{96}$ preferably is hydrogen or $R^{98}$—$(C_1–C_8)$-alkyl-, more preferably hydrogen or $R^{98}$—$(C_1–C_4)$-alkyl. Particularly preferably, $R^{96}$ is hydrogen. $R^{98}$ preferably is hydroxycarbonyl-, $(C_1–C_8)$-alkyloxycarbonyl-, or aminocarbonyl-, more preferably hydroxycarbonyl-, $(C_1–C_4)$-alkyloxycarbonyl-, or aminocarbonyl-.

$R^{97}$ preferably is $R^{99}$—$(C_1–C_8)$-alkyl- or $R^{99}$—$(C_6–C_{14})$-aryl-$(C_1–C_4)$-alkyl-. More preferably, $R^{97}$ is $R^{99}$—$(C_1–C_8)$-alkyl-. As explained above with respect to alkyl groups in general, a $(C_1–C_8)$-alkyl present in the $R^{97}$ group can be saturated or unsaturated and can be acyclic or cyclic. Preferably, such an alkyl group is a saturated acyclic alkyl group or a saturated cyclic alkyl group (=cycloalkyl group) or a saturated group of the type cycloalkyl-alkyl-, more preferably a saturated acyclic alkyl group or saturated cycloalkyl group, particularly preferably a saturated acyclic alkyl group. If the $(C_1–C_8)$-alkyl present in the $R^{97}$ group is a saturated acyclic alkyl group, the $R^{97}$ group preferably is the $R^{99}$—$(C_1–C_4)$-alkyl- group wherein $(C_1–C_4)$-alkyl is a saturated acyclic alkyl, more preferably one of the $R^{99}$—$CH_2$—, $R^{99}$—$CH_2$—$CH_2$—, $R^{99}$—$CH_2$—$CH_2$—$CH_2$—, or $R^{99}$—$CH_2$—$CH_2$—$CH_2$—$CH_2$— groups, particularly preferably the $R^{99}$—$CH_2$—$CH_2$— group. If the $(C_1–C_8)$-alkyl present in the $R^{97}$ group is a saturated cyclic alkyl group, the $R^{97}$ group preferably is the $R^{99}$—$(C_3–C_7)$-cycloalkyl-group, more preferably the $R^{99}$—$(C_3–C_6)$-cycloalkyl-group, wherein the cycloalkyl group is saturated, particularly preferably the $R^{99}$-cyclopropyl-, $R^{99}$-cyclopentyl-, or $R^{99}$-cyclohexyl- group. In a group like $R^{99}$—$(C_3–C_7)$-cycloalkyl-, for example, $R^{99}$-cyclopropyl-, $R^{99}$-cyclopentyl-, or $R^{99}$-cyclohexyl-, the $R^{99}$ group can be present in any desired position of the cycloalkyl group, in the case of a cyclopropyl group for example, in the 2-position, in the case of a cyclopentyl group, for example, in the 2-position or 3-position, in the case of a cyclohexyl group for example, in the 2-position, the 3-position, or the 4-position where the 4-position is preferred. Particularly preferred $R^{97}$ groups are the $R^{99}$—$CH_2$—$CH_2$— and 2-$(R^{99})$-cyclopropyl groups, especially preferred is the $R^{99}$—$CH_2$—$CH_2$— group.

$R^{99}$ preferably is hydroxycarbonyl-, $(C_1–C_8)$-alkyloxycarbonyl-, $(C_6–C_{14})$-aryl-$(C_1–C_4)$-alkyloxycarbonyl, aminocarbonyl-, $(C_1–C_8)$-alkylaminocarbonyl-, or another derivative or protected form of a hydroxycarbonyl group like an ester or an amide as described above. More preferably, $R^{99}$ is hydroxycarbonyl-, $(C_1–C_8)$-alkyloxycarbonyl-, $(C_6–C_{14})$-aryl-$(C_1–C_4)$-alkyloxycarbonyl, aminocarbonyl-, or $(C_1–C_8)$-alkylaminocarbonyl-, particularly preferably hydroxycarbonyl-, $(C_1–C_8)$-alkyloxycarbonyl-, aminocarbonyl-, or $(C_1–C_8)$-alkylaminocarbonyl. Most preferably, $R^{99}$ is hydroxycarbonyl- or $(C_1–C_8)$-alkyloxycarbonyl-. A $(C_1–C_8)$-alkyloxy- group present in the $R^{99}$ group preferably is a $(C_1–C_4)$-alkyloxy- group. An alkyl group present in the $R^{99}$ group preferably is a saturated acyclic group.

Preferred compounds of formula I are those compounds in which one or more of the residues have preferred denotations or have one or more specific denotations of the denotations listed in their respective definitions and in the general explanations on the respective residues, all combinations of such preferred meanings and specific denotations being a subject of the present invention. Also all preferred compounds of formula I are a subject of the present invention in any stereoisomeric form or mixture thereof in any ratio, or in the form of a physiologically tolerable salt thereof. Further, all preferred compounds of formula I are a subject of the present invention in the form of their prodrugs and other derivatives as explained above, for example, in the form of their esters such as $(C_1-C_4)$-alkyl and other esters and their amides such as unsubstituted amides, $(C_1-C_4)$-alkyl amides, and other amides.

For example, preferred compounds of formula I are compounds in which:

$R^1$ is $R^{11}$—CO—;
$R^{91}$ is hydrogen;
r is 0 or 1;
s is 0, 1, or 2;
t is 0;
$R^{94}$ is selected from chlorine and fluorine;
$R^{95}$ is amidino or $((C_1-C_4)$-alkyl)oxycarbonylamidino- and the $R^{95}$ group is bonded in the 4-position of the phenyl ring in formula I;
in any stereoisomeric form or mixture thereof in any ratio, or a physiologically tolerable salt thereof.

Compounds of this type contain a structural unit which is derived from 4-amidinophenylglycine or 4-amidinophenylalanine which is optionally substituted in the amidino group with a $((C_1-C_4)$-alkyl)oxycarbonyl- group, and optionally substituted in the phenyl group with chlorine and/or fluorine, and substituted in the N-terminal amino group with a $R^{11}$—CO— group. In a particularly preferred group of these compounds, s is 0 and the amidino group is not substituted, i.e., particularly preferred compounds of this type are derived from 4-amidinophenylglycine or 4-amidinophenylalanine, especially preferred compounds from 4-amidinophenylalanine, which are substituted in the N-terminal amino group with a $R^{11}$—CO— group.

Preferred compounds of formula I are also compounds in which:

$R^{92}$ and $R^{96}$ are hydrogen;
$R^{97}$ is $R^{99}$—$CH_2$—$CH_2$—;
$R_{99}$ is hydroxycarbonyl- or $((C_1-C_8)$-alkyl)oxycarbonyl-;
in any stereoisomeric form or mixture thereof in any ratio, or a physiologically tolerable salt thereof.

Compounds of this type contain a structural unit which is a glutamic acid residue or derivative thereof wherein the carboxylic acid group in the side chain is converted into a $(C_1-C_8)$-alkyl ester.

A set of particularly preferred compounds of formula I is formed by compounds in which:

r is 1;
s is 0;
t is 0;
$R^1$ is allyloxycarbonyl-;
$R^{95}$ is amidino which is bonded in the 4-position of the phenyl ring in formula I;
$R^{91}$, $R^{92}$, $R^{93}$, and $R^{96}$ are hydrogen;
$R^{97}$ is $R^{99}$—$CH_2$—$CH_2$—;
$R^{99}$ is hydroxycarbonyl- or $((C_1-C_4)$-alkyl)oxycarbonyl-;
in any stereoisomeric form or mixture thereof in any ratio, or a physiologically tolerable salt thereof.

A further set of particularly preferred compounds is formed by compounds of formula I in which:

r is 1;
s is 0 or 1;
t is 0;
$R^1$ is allyloxycarbonyl-;
$R^2$ is $R^{21}(R^{22})$CH—, $R^{23}$—Het-$(CH_2)_k$—, or $R^{23}(R^{24})$N—$(CH_2)_m$—D—$(CH_2)_n$—;

D is a divalent —$C(R^{31})(R^{32})$— residue, a divalent phenylene residue, or a divalent residue derived from an aromatic monocyclic Het group;
$R^{94}$ is haloen;
$R^{95}$ is amidino or $((C_1-C_4)$-alkyl)oxycarbonylamidino- and is bonded in the 4-position of the phenyl ring in formula I;
$R^{91}$, $R^{92}$, $R^{93}$, and $R^{96}$ are hydrogen;
$R^{97}$ is $R^{99}$—$CH_2$—$CH_2$—;
$R^{99}$ is hydroxycarbonyl- or $((C_1-C_4)$-alkyl)oxycarbonyl-;
in any stereoisomeric form or mixture thereof in any ratio, or a physiologically tolerable salt thereof.

Further, preferred compounds of formula I are compounds in which chiral centers are present in substantially uniform configuration. Particularly preferably, the chiral carbon atom to which the $R^1(R^{91})$N— and —$(CH_2)_r$— groups are bonded has S configuration, i.e., the structural unit $R^1(R^{91})$N—CH(—$(CH_2)_r$-(substituted phenyl))—CO— is preferably derived from an L-amino acid derivative. If $R^{96}$ is hydrogen, particularly preferably the chiral carbon atom to which the $R^{96}$ and $R^{97}$ groups are bonded has S configuration, i.e., the structural unit —$(R^{92})$N—CH$(R^{97})$—CO— is preferably derived from an L-amino acid derivative.

The present invention also relates to processes of preparation by which compounds of formula I are obtainable. Compounds of formula I can generally be prepared by linkage of two or more fragments (or building blocks) which can be derived retrosynthetically from formula I. In the preparation of compounds of formula I, it can generally be advantageous or necessary in the course of the synthesis to introduce functional groups which could lead to undesired reactions or side reactions in a synthesis step in the form of precursors which are later converted into the desired functional groups, or to temporarily block functional groups by a protective group strategy suited to the synthesis problem. Such strategies are well known to those skilled in the art (see, for example, Greene and Wuts, *Protective Groups in Organic Synthesis*, 2nd ed., John Wiley and Sons (1991)). As examples of precursor groups, nitro groups may be mentioned which can later be converted by reduction, for example, by catalytic hydrogenation, into amino groups, or cyano groups may be mentioned which may later be converted into amidino groups or, by reduction, into aminomethyl groups. Protecting groups (or blocking groups) that may be present on functional groups include allyl, tert-butyl, benzyl, tert-butyloxycarbonyl (Boc), benzyloxycarbonyl (Z), and 9-fluorenylmethyloxycarbonyl (Fmoc) as protecting groups for hydroxy, carboxylic acid, amino, guanidino, and amidino groups.

In particular, in the preparation of compounds of formula I, building blocks are connected by performing one or more amide couplings (or condensations), i.e., by forming amide bonds between a carboxylic acid group (or a similar group like a sulfonic acid group) of one building block and an amino group (or a similar group) of another building block. For example, compounds of formula I can be prepared by linking the building blocks of formulae II, III, and IV by means of forming in a manner known per se an amide bond between the carboxylic acid derivative CO—$Y^1$ group depicted in formula II and the nitrogen atom depicted in formula III and by forming a further amide bond between the carboxylic acid derivative CO—$Y^2$ depicted in formula III and the nitrogen atom depicted in formula IV.

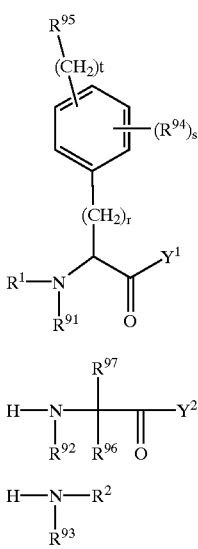

In compounds of formulae II, III, and IV, $R^1$, $R^2$, $R^{91}$, $R^{92}$, $R^{93}$, $R^{94}$, $R^{95}$, $R^{96}$, $R^{97}$, r, s, and t are defined as above, but functional groups in these compounds can also be present in the form of precursor groups which are later converted into the groups present in compounds of formula I, or functional groups can be present in protected form. $Y^1$ and $Y^2$ which can be identical or different are hydroxy or other nucleophilically substitutable leaving groups, i.e., the $CO$—$Y^1$ and $CO$—$Y^2$ groups in compounds of formulae II and III are carboxylic acid COOH groups or activated derivatives of carboxylic acids such as, for example, acid chlorides, esters like ($C_1$–$C_4$)-alkyl esters or activated esters, or mixed anhydrides.

The starting compounds of formulae II, III, and IV, and other compounds which are employed in the synthesis of compounds of formula I for introducing certain structural units, are commercially available or can be readily prepared from commercially available compounds by, or analogously to, procedures described below or in the literature which is readily available to one skilled in the art.

For the preparation of compounds of formula I, compounds of formulae II and III may be condensed and the resulting intermediate product is then condensed with a compound of formula IV to give a compound of formula I, or compounds of formulae III and IV may be condensed and the resulting intermediate product is then condensed with a compound of formula II to give a compound of formula I. After any such step in the course of such syntheses, protecting and deprotecting steps and conversions of precursor groups into the desired final groups may be carried out and further modifications may be made. For example, a group like $R^1$ that is different from hydrogen may already be present in the compound of formula II, which is employed into the coupling reaction with the compound of formula III or with the intermediate obtained from compounds of formulae III and IV, but the $R^1$ group may also be introduced only after performing one coupling reaction or both coupling reactions. The synthetic strategy for the preparation of a compound of formula I can thus be varied broadly, and it depends on the individual case which synthetic procedure is preferred.

Various general methods for the formation of an amide bond that can be employed in the synthesis of compounds of formula I are known to those skilled in the art, for example, from peptide chemistry. The coupling step can be carried out by employing a free carboxylic acid, i.e., a compound of formulae II or III or an intermediate coupling product in which a $CO$—$Y^1$ or $CO$—$Y^2$ group reacting in that step is a COOH group, activating that carboxylic acid group, preferably in situ, by means of a customary coupling reagent such as a carbodiimide like dicyclohexylcarbodiimide (DCC) or diisopropylcarbodiimide (DIC), or a carbonyidiazole like carbonyldiimidazole, or a uronium salt like O-((cyano-(ethoxycarbonyl)-methylene)amino)-1,1,3,3-tetramethyluronium tetrafluoroborate (TOTU) or O-(7-azabenzotriazol-1-yl)-N,N,N',N'-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound. An amide bond can also be formed by reacting an amino compound with a carboxylic acid halide, in particular a carboxylic acid chloride, which can be prepared in a separate step or in situ from a carboxylic acid and, for example, thionyl chloride, or a carboxylic acid ester or thioester, for example, a methyl ester, ethyl ester, phenyl ester, nitrophenyl ester, pentafluorophenyl ester, methylthio ester, phenylthio ester, or 2-pyridylthio ester, i.e., with a compound of formula II or III or with an intermediate coupling product in which $Y^1$ or $Y^2$ is Cl, methoxy, ethoxy, optionally substituted phenyloxy, methylthio, phenylthio, or 2-pyridylthio.

The activation reactions and coupling reactions are usually performed in the presence of an inert solvent (or diluent), for example, in the presence of an aprotic solvent like dimethylformamide (DMF), tetrahydrofuran (THF), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and may be, for example, from about −20° C. to the boiling temperature of the solvent or diluent. Also depending on the specific process, it may be necessary or advantageous to add in a suitable amount of one or more auxiliary agents, for example, a base like a tertiary amine, such as triethylamine or diisopropylethylamine, or an alkali metal alcoholate, such as sodium methoxide or potassium tert-butoxide, for adjusting the pH or for neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds as well as source literature are given in various standard references like, for example, J. March, *Advanced Organic Chemistry*, 4th ed., John Wiley & Sons (1992); or Houben-Weyl, *Methoden der Organischen Chemie* (Methods of Organic Chemistry), Georg Thieme Verlag.

Protective groups that may still be present in the products obtained in the coupling reaction are then removed by standard procedures. For example, tert-butyl protecting groups, in particular a tert-butyl ester group which is a protected form of a COOH group, can be deprotected, i.e., converted into the carboxylic acid group in the case of an ester, by treatment with trifluoroacetic acid. Benzyl groups can be removed by hydrogenation. Fluorenylmethoxycarbonyl groups can be removed by secondary amines like piperidine. As already explained, after the coupling reaction also functional groups can be generated from suitable precursor groups or, if desired, further reactions can be carried out on the coupling products by standard processes, for example, acylation reactions or esterification reactions. In addition, a conversion into a physiologically tolerable salt or a prodrug of a compound of formula I can then be carried out by known processes.

As examples of the introduction of specific functional groups, procedures for the introduction of amidino groups and guanidino groups may be explained, which amidino groups and guanidino groups are represented, for example, by the $R^{95}$ group. Amidines can be prepared from cyano compounds by addition of an alcohol under acidic anhydrous conditions, for example, in methanol or ethanol saturated with hydrogen chloride, and subsequent ammonolysis. A further method of preparing amidines is the addition of hydrogen sulfide to the cyano group, followed by methylation of the resulting thioamide, and subsequent reaction with ammonia. Another method is the addition of hydroxylamine to the cyano group which leads to a hydroxyamidine. If desired, the N—O bond in the hydroxyamidine can be cleaved, for example, by catalytic hydrogenation, to give the amidine.

An amino group which may be obtained from a nitro precursor group can be converted into a guanidino or nitroguanidino group in which latter group the nitro group is a protecting group. For the guanylation or nitroguanylation of an amino group, the following reagents can be used which are well known to one skilled in the art and which are all described in the literature: O-methylisourea, S-methylisothiourea, nitro-S-methylisothiourea, formamidinesulfonic acid, 3,5-dimethyl-1-pyrazolylformamidinium nitrate, N,N'-di-tert-butyloxycarbonyl-S-methylisothiourea, or N-alkyloxycarbonyl- and N,N'-dialkyloxycarbonyl-S-methylisothiourea.

In general, a reaction mixture containing a final compound of formula I or an intermediate is worked up and, if desired, the product is then purified by customary processes known to those skilled in the art. For example, a synthesized compound can be purified using well known methods such as crystallization, chromatography, or reverse phase-high performance liquid chromatography (RP-HPLC), or other methods of separation based, for example, on the size, charge, or hydrophobicity of the compound. Similarly, well known methods such as amino acid sequence analysis, NMR, IR, and mass spectrometry (MS) can be used for characterizing a compound of the invention.

The reactions described above and below that are carried out in the syntheses of compounds of formula I can generally be carried out according to the methods of conventional solution phase chemistry as well as according to the methods of solid phase chemistry which both are customarily applied in peptide synthesis. Among the various strategies that may be employed if compounds of formula I are to be prepared on solid phase, the following strategy for the preparation of compounds in which a hydroxycarbonyl group is present in the $R^{96}$ group or the $R^{97}$ group may be mentioned. As starting material, a compound of formula Fmoc-HN—C($R^{96}$)($R^{97}$)—CO—OPG is employed in which Fmoc is 9-fluorenylmethoxycarbonyl, PG is a carboxylic acid protecting group, and $R^{96}$ and $R^{97}$ are defined as above with the proviso that a free hydroxycarbonyl COOH group is present in one of the $R^{96}$ and $R^{97}$ groups. Said starting compound is attached to a Wang resin (S. S. Wang, J. Am. Chem. Soc. 95 (1973) 1328) by coupling the COOH group to the resin. Then the Fmoc protecting group is cleaved off and a compound of formula II is coupled to the amino group. Subsequently, the PG protecting group is cleaved off and the resulting carboxylic acid group is coupled to a compound of formula IV. Finally, the compound is cleaved off from the resin with trifluoroacetic acid. When solid phase synthesis methods are used, functional groups that are present can be modified or functional groups can be introduced into the nascent compound while it is attached to the resin or after the compound has been cleaved off from the resin to obtain, for example, an N-terminal derivative such as an N-terminal allyloxycarbonylated compound or a derivative of a carboxy group which group can, for example, be amidated. A compound of the invention may also be synthesized by combining steps performed according to the methods of solution phase organic chemistry and steps performed according to the methods of solid phase organic chemistry. A compound of the invention can also be synthesized using an automated synthesizer.

Compounds of the present invention inhibit the activity of the blood coagulation enzyme factor VIIa. In particular, they are specific inhibitors of factor VIIa. As used herein, the term specific when used in reference to the inhibition of factor VIIa activity means that a compound of formula I can inhibit factor VIIa activity without substantially inhibiting the activity of other specified proteases involved in the blood coagulation and/or the fibrinolysis pathway including, for example, factor Xa, plasmin, and thrombin (using the same concentration of the inhibitor). The activity of compounds of formula I can be determined, for example, in the assays described below or in other assays known to those skilled in the art. Preferred compounds of the present invention are those compounds which have a $Ki \leq 10$ $\mu M$, particularly preferably $\leq 1$ $\mu M$, for factor VIIa inhibition as determined in the assay described below, and which preferably do not substantially inhibit the activity of other proteases involved in coagulation and fibrinolysis relative to the inhibition of factor VIIa (using the same concentration of the inhibitor). Compounds of the invention inhibit factor VIIa catalytic activity either directly, within the prothrombinase complex or as a soluble subunit, or indirectly, by inhibiting the assembly of factor VIIa into the prothrombinase complex.

Because of their factor VIIa inhibitory activity, compounds of formula I are useful pharmacologically active compounds which are suitable, for example, for influencing blood coagulation (or clotting) and fibrinolysis, and for the therapy and prophylaxis of, for example, cardiovascular disorders, thromboembolic diseases, or restenoses. Compounds of formula I or a physiologically tolerable salt or prodrug thereof can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which contain, as an active constituent, an effective amount of at least one compound of formula I and/or a physiologically tolerable salt and/or a prodrug thereof in addition to at least one pharmaceutically acceptable carrier.

The present invention therefore also relates to compounds of formula I and/or a physiologically tolerable salt and/or a prodrug thereof for use as pharmaceuticals (or medicaments), to the use of compounds of formula I and/or a physiologically tolerable salt and/or a prodrug thereof for the production of pharmaceuticals for the inhibition of factor VIIa, or for influencing blood coagulation or fibrinolysis, or for the therapy or prophylaxis of the diseases mentioned above or below, for example, for the production of pharmaceuticals for the therapy and prophylaxis of cardiovascular disorders, thromboembolic diseases, or restenoses. The invention also relates to the use of compounds of formula I and/or a physiologically tolerable salt and/or a prodrug thereof for the inhibition of factor VIIa, or for influencing blood coagulation or fibrinolysis, or for the therapy or prophylaxis of the diseases mentioned above or below, for example, for use in the therapy and prophylaxis of cardiovascular disorders, thromboembolic diseases, or restenoses, and to methods of treatment aiming at such purposes including methods for said therapies and prophylaxes. The present invention furthermore relates to pharmaceutical preparations (or pharmaceutical compositions) which contain an effective amount of at least one compound of formula I and/or a physiologically tolerable salt and/or a prodrug thereof in addition to at least one pharmaceutically acceptable carrier, i.e., one or more pharmaceutically acceptable carrier substances (or vehicles) and/or additives (or excipients).

The pharmaceuticals can be administered orally, for example, in the form of pills, tablets, lacquered tablets, coated tablets, granules, hard and soft gelatin capsules, solutions, syrups, emulsions, suspensions, or aerosol mixtures. Administration, however, can also be carried out rectally, for example, in the form of suppositories, or parenterally, for example, intravenously, intramuscularly, or subcutaneously, in the form of injection solutions or infusion solutions, microcapsules, implants, or rods, or percutaneously or topically, for example, in the form of ointments, solutions, or tinctures, or in other ways, for example, in the form of aerosols or nasal sprays.

The pharmaceutical preparations according to the invention are prepared in a manner known per se and familiar to one skilled in the art, pharmaceutically acceptable inert inorganic and/or organic carrier substances being used in addition to the compound(s) of formula I and/or its (their) physiologically tolerable salts and/or its (their) prodrugs. For the production of pills, tablets, coated tablets, and hard gelatin capsules it is possible to use, for example, lactose, corn starch or derivatives thereof, talc, or stearic acid or its salts. Carrier substances for soft gelatin capsules and suppositories are, for example, fats, waxes, semisolid and liquid polyols, or natural or hardened oils. Suitable carrier substances for the production of solutions, for example, injection solutions, or of emulsions or syrups are water, saline, alcohols, glycerol, polyols, sucrose, invert sugar, glucose, or vegetable oils. Suitable carrier substances for microcapsules, implants, or rods are, for example, copolymers of glycolic acid and lactic acid. The pharmaceutical preparations normally contain about 0.5 to about 90% by weight of compounds of formula I and/or a physiologically tolerable salt and/or a prodrug thereof. The amount of the active ingredient of formula I and/or a physiologically tolerable salt and/or a prodrug thereof in the pharmaceutical preparations normally is from about 0.5 to about 1000 mg, preferably from about 1 to about 500 mg.

In addition to the active ingredients of formula I and/or a physiologically acceptable salt and/or a prodrug thereof and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents, or antioxidants. They can also contain two or more compounds of formula I and/or a physiologically tolerable salt and/or a prodrug thereof. If a pharmaceutical preparation contains two or more compounds of formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in compounds of formula I allows a great deal of control over the biological and physicochemical properties of the compounds and thus allows the selection of such desired compounds. Furthermore, in addition to at least one compound of formula I and/or a physiologically tolerable salt and/or a prodrug thereof, the pharmaceutical preparations can also contain at least one other therapeutically or prophylactically active ingredient.

As inhibitors of factor VIIa, compounds of formula I and their physiologically tolerable salts and their prodrugs are generally suitable for the therapy and prophylaxis of conditions in which the activity of factor VIIa plays a role or has an undesired extent, or which can favorably be influenced by inhibiting factor VIIa or by decreasing its activity, or for the prevention, alleviation, or cure of which an inhibition of factor VIIa or a decrease in its activity is desired by the physician. As inhibition of factor VIIa influences blood coagulation and fibrinolysis, compounds of formula I and their physiologically tolerable salts and their prodrugs are generally suitable for reducing blood clotting, or for the therapy and prophylaxis of conditions in which the activity of the blood coagulation system plays a role or has an undesirable effect, or which can favorably be influenced by reducing blood clotting, or for the prevention, alleviation, or cure of conditions in which a decreased activity of the blood coagulation system is desired by the physician. A specific subject of the present invention, thus, is the reduction or inhibition of unwanted blood clotting, in particular in an individual, by administering an effective amount of a compound I or a physiologically tolerable salt or a prodrug thereof, as well as pharmaceutical preparations therefor.

Conditions in which a compound of formula I can be favorably used include, for example, cardiovascular disorders, thromboembolic diseases, or complications associated, for example, with infection or surgery. Compounds of the present invention can also be used to reduce an inflammatory response. Examples of specific disorders for the treatment or prophylaxis of which compounds of formula I can be used are coronary heart disease, myocardial infarction, angina pectoris, vascular restenosis, for example, restenosis following angioplasty like PTCA, adult respiratory distress syndrome, multi-organ failure, stroke, and disseminated intravascular clotting disorder. Examples of related complications associated with surgery are thromboses, like deep vein and proximal vein thrombosis, which can occur following surgery. In view of their pharmacological activity, compounds of the invention can replace other anticoagulant agents such as heparin. The use of a compound of the invention can result, for example, in a cost saving as compared to other anticoagulants.

When using compounds of formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example, 2, 3, or 4, part administrations. As usual, depending on individual behavior it may be necessary to deviate upwards or downwards from the daily dose indicated.

A compound of formula I can also advantageously be used as an anticoagulant outside an individual. For example, an effective amount of a compound of the invention can be contacted with a freshly drawn blood sample to prevent coagulation of the blood sample. Further, a compound of formula I and its salts can be used for diagnostic purposes, for example, in in vitro diagnoses, and as an auxiliary in biochemical investigations. For example, a compound of formula I can be used in an assay to identify the presence of factor VIIa or to isolate factor VIIa in a substantially purified form. A compound of the invention can be labeled, for example, with a radioisotope, and the labeled compound bound to factor VIIa is then detected using a routine method useful for detecting the particular label. Thus, a compound of formula I or a salt thereof can be used advantageously as a probe to detect the location or amount of factor VIIa activity in vivo, in vitro, or ex vivo.

Furthermore, compounds of formula I can be used as synthesis intermediates for the preparation of other compounds, in particular of other pharmaceutical active ingredients, which are obtainable from compounds of formula I, for example, by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

| Abbreviations | |
|---|---|
| Allyloxycarbonyl | Alloc |
| L-4-Amidinophenylalanyl | pAph |
| L-Aspartyl | Asp |
| tert-Butyl | tBu |
| Dichloromethane | DCM |
| N,N'-Diisopropylcarbodiimide | DIC |
| N,N-Diisopropyl-N-ethylamine | DIEA |
| N,N-Dimethylformamide | DMF |
| Dimethylsulfoxide | DMSO |
| N-Ethylmorpholine | NEM |
| 9-Fluorenylmethyloxycarbonyl | Fmoc |
| L-Glutamyl | Glu |
| N-Hydroxybenzotriazole | HOBt |
| Pentafluorophenyl | Pfp |
| Tetrahydrofuran | THF |
| Trifluoroacetic acid | TFA |
| O-((cyan(ethoxycarbonyl)methylene)amino)-1,1,3,3-tetramethyluronium tetrafluoroborate | TOTU |
| O-(7-azabenzotriazol-1-yl)-1,1,3,3-tetramethyluronium hexafluorophosphate | HATU |

Compounds of formula I are named according to the rules of peptide chemistry. Thus, for example, a name like Alloc-pAph-Glu-(4-aminobenzyl)amide means that in the respective compound an L-4-amidinophenylalanyl unit is bonded via a peptide bond to an L-glutamyl unit and that the α-amino group of the L-4-amidinophenylalanyl unit carries an allyloxycarbonyl group, and that in the 1-position of the glutamyl unit instead of a free carboxylic acid group an N-(4-aminobenzyl)carboxamide group is present, i.e., that the respective compound has the following structural formula.

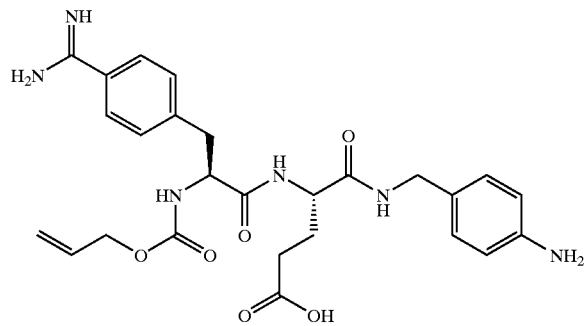

When, in the final step of the synthesis of a compound, an acid such as trifluoroacetic acid or acetic acid was used, for example, when trifluoroacetic acid was employed to remove a tert-butyl group or when a compound was purified by chromatography using an eluent which contained such an acid, in some cases, depending on the work-up procedure, for example, the details of a freeze-drying process, the compound was obtained partially or completely in the form of a salt of the acid used, for example, in the form of the acetic acid salt or trifluoroacetic acid salt.

Example 1

Alloc-pAph-Glu-(4-aminobenzyl)amide a) (S)-2-Allyloxycarbonylamino-3-(4-cyanophenyl) propionic Acid A suspension of 50 g (0.221 mol) of (S)-2-amino-3-(4-cyanophenyl)propionic acid in 150 ml of water was adjusted to pH=8 with 1N NaOH. 26.6 g (0.221 mol) of allylchloroformate in 225 ml of dioxane were slowly added at 0 to 5° C. (pH kept at 8 by addition of 1N NaOH). After completion of the reaction (thin layer chromatography (TLC) control) the mixture was extracted with DCM and the aqueous layer was acidified to pH=2 with KHSO$_4$. The precipitate was dissolved in DCM, dried (Na$_2$SO$_4$), and evaporated. The residue was recrystallized from ether/petroleum benzene to give 31 g (51%) of the title compound. MS=275.1 (M+1)$^+$.

b) (S)-2-Allyloxycarbonylamino-3-(4-carbamimidoylphenyl)propionic Acid Ethyl Ester Hydrochloride (Alloc-pAph-OC$_2$H$_5$ Hydrochloride)

Dried gaseous hydrochloric acid was passed through a solution of 15 g (0.055 mol) of (S)-2-allyloxycarbonylamino-3-(4-cyanophenyl)propionic acid in 200 ml of ethanol. After 5 h the mixture was kept overnight at 0° C. The solvent was evaporated and the residue was treated with 250 ml of a 3M solution of ammonia in ethanol for 12 h at room temperature (RT). The solvent was evaporated and the residue was washed with DCM and crystallized with ether to give 17.5 g (90%) of the title compound. MS=320.3 (M+1)$^+$.

c) (S)-2-Allyloxycarbonylamino-3-(4-carbamimidoylphenyl)propionic Acid Hydrochloride (Alloc-pAph-OH Hydrochloride)

17 g (0.048 mol) of (S)-2-allyloxycarbonylamino-3-(4-carbamimidoylphenyl)propionic acid ethyl ester hydrochloride were treated with 400 ml of half-concentrated hydrochloric acid for 3 h at RT. The solvent was evaporated (<30° C.) and the residue was stirred with ether. Yield=15 g (95%). MS=292.2 (M+1)$^+$.

d) Alloc-pAph-Glu(OtBu)—OCH$_3$ Hydrochloride

To a solution of 1.3 g (3.97 mmol) of Alloc-pAph-OH hydrochloride and 1.0 g (3.97 mmol) of H-Glu(OtBu)—

OCH₃ hydrochloride in 15 ml of DMF was added 1.63 g (4.96 mmol) of TOTU and 1.14 g (9.9 mmol) of NEM. After 5 h at RT the solution was poured into 150 ml of brine and extracted with DCM. The organic layer was dried (Na₂SO₄) and evaporated to give 1.7 g (81%) of the title compound. MS=491.2 (M+1)⁺.

e) Alloc-pAph-Glu(OtBu)—OH 1.7 g (3.17 mmol) of Alloc-pAph-Glu(OtBu)—OCH₃ hydrochloride in 15 ml of THF and 50 ml of water were treated with 0.16 g (3.8 mmol) of lithium hydroxide monohydrate. After 3 h the solvent was removed and the residue freeze dried to give 1.25 g (82%) of the title compound. MS=477.5 (M+1)⁺.

f) Alloc-pAph-Glu(OtBu)-(4-aminobenzyl)amide

To a solution of 56 mg (0.12 mmol) of Alloc-pAph-Glu (OtBu)—OH and 13 μl (0.12 mmol) of p-aminobenzylamine in 10 ml of DMF was added 39 mg (0.12 mmol) of TOTU and 15 μl (0.12 mmol) of NEM at 3° C. After 12 h at RT the solvent was removed to give 0.15 g of the title compound which was used for the next step without further purification. MS=581.4 (M+1)⁺.

g) Alloc-pAph-Glu-(4-aminobenzyl)amide 150 mg of Alloc-pAph-Glu(OtBu)-4-aminobenzylamide were treated with 1 ml of 90% TFA. After 12 h ethyl acetate/DCM/methanol was added and the precipitate was filtered and dried to give 55 mg of the title compound. MS=525.3 (M+1)⁺.

Example 2

Alloc-pAph-Glu-(3-aminobenzyl)amide

To a solution of 30 mg (0.064 mmol) of Alloc-pAph-Glu (OtBu)—OH and 8 mg (0.064 mmol) of 3-aminobenzylamine in 5 ml of DMF was added 21 mg (0.064 mmol) of TOTU and 8 μl (0.064 mmol) of NEM at 3° C. After 12 h at RT the solvent was removed and the residue was treated with 1 ml of 90% TFA. After 8 h at RT ethyl acetate was added and the precipitate was filtered and dried to give 30 mg of the title compound. MS=525.4 (M+1)⁺.

Example 3

Alloc-pAph-Glu-(2-(4-aminophenyl)ethyl)amide

To a solution of 30 mg (0.064 mmol) of Alloc-pAph-Glu (OtBu)—OH and 8.5 μl (0.064 mmol) of 2-(4-aminophenyl) ethylamine in 4 ml of DMF was added 21 mg (0.064 mmol) of TOTU and 8 μl (0.064 mmol) of NEM at 3° C. After 12 h at RT the solvent was removed and the residue was treated with 1 ml of 90% TFA. After 8 h at RT ethyl acetate was added and the precipitate was filtered and dried to give 30 mg of the title compound. MS=539.4 (M+1)⁺.

Example 4

Alloc-pAph-Glu-(2,4-dihydroxybenzyl)amide

To a solution of 30 mg (0.064 mmol) of Alloc-pAph-Glu (OtBu)—OH and 14 mg (0.064 mmol) of 3,4-dihydroxybenzylamine in 5 ml of DMF was added 21 mg (0.064 mmol) of TOTU and 16 μl (0.128 mmol) of NEM at 3° C. After 12 h at RT the solvent was removed and the residue was treated with 1 ml of 90% TFA. After 8 h at RT ethyl acetate was added and the precipitate was filtered and dried to give 45 mg of the title compound. MS=542.4 (M+1)⁺.

Example 5

Alloc-pAph-Glu-(2-aminobenzyl)amide

To a solution of 59 mg (0.124 mmol) of Alloc-pAph-Glu (OtBu)—OH and 15 mg (0.124 mmol) of 2-aminobenzylamine in 1.5 ml DMF was added 41 mg (0.124 mmol) of TOTU and 28 mg (0.248 mmol) of NEM at 3° C. After 12 h at RT the solvent was removed and the residue was treated with 1 ml of 90% TFA. After 8 h at RT the solvent was evaporated and the residue was purified by HPLC to give 1.5 mg of the title compound. MS=525.4 (M+1)⁺.

Example 6

Alloc-pAph-Glu-((RS)-2-amino-9H-fluorene-9-yl) amide

To a solution of 60 mg (0.126 mmol) of Alloc-pAph-Glu (OtBu)—OH and 34 mg (0.126 mmol) of (RS)-2,9-diamino-9H-fluorene in 5 ml DMF was added 42 mg (0.126 mmol) of TOTU and 32 μl (0.252 mmol) of NEM at 3° C. After 12 h at RT the solvent was removed and the residue was treated with 1 ml of 90% TFA. After 8 h at RT ethyl acetate was added and the precipitate was filtered and dried to give 50 mg of the title compound. MS=598.7 (M+1)⁺.

Example 7

Alloc-pAph-Glu-(3-ethoxycarbonylaminopropyl) amide a) 3-Ethoxycarbonylaminopropylamine To a solution of 0.5 g (2.9 mmol) of 3-tert-butyloxycarbonylaminopropylamine in 8 ml of DCM and 0.37 g (2.9 mmol) of NEM was added a solution of 0.32 g (0.29 mmol) of ethyl chloroformate in 2 ml of DCM. After 24 h at RT the mixture was washed with water and dried. The solvent was evaporated and the residue was stirred with 5 ml of TFA (90%). After 1 h the solvent was evaporated to give 0.6 g of the title compound. MS=147.0 (M+1)⁺.

b) Alloc-pAph-Glu-(3-ethoxycarbonylaminopropyl)amide

To a solution of 59 mg (0.124 mmol) of Alloc-pAph-Glu (OtBu)—OH and 16 mg (0.124 mmol) of 3-ethoxycarbonylaminopropylamine in 1.5 ml of DMF was added 41 mg (0.124 mmol) of TOTU and 28 mg (0.248 mmol) of DIEA at 3° C. After 12 h at RT the solvent was removed and the residue was treated with 1 ml of 90% TFA. After 8 h at RT the solvent was evaporated and the residue was purified by HPLC to give 1.4 mg of the title compound. MS=549.2 (M+1)⁺.

Example 8

Alloc-pAph-Glu-((R)-1-(3-aminophenyl)ethyl)amide and Alloc-pAph-Glu-((S)-1-(3-aminophenyl)ethyl) amide a) (RS)-3-(1-Aminoethyl)phenylamine Hydrochloride A mixture of 0.69 g (5.123 mmol) of 1-(3-amino-phenyl)-ethanone, 0.43 g (6.15 mmol) of hydroxylamine, 0.50 g (6.15 mmol) of sodium acetate, and 15 ml of ethanol was heated at 80° C. for 8 h. The solvent was removed and the residue was distributed between water and ethyl acetate. The organic phase was dried, filtered, and the solvent was evaporated to give 0.53 g of the oxime (MS=151.2 (M+1)⁺). 0.53 g of the oxime were dissolved in 100 ml of methanol and hydrogenated in a Parr apparatus at RT. After 2 days the mixture was filtered through celite and the solvent was evaporated. The residue was stirred with ether saturated with hydrogen chloride. The solvent was evaporated to give 0.46 g of the title compound. MS=137.1 (M+1)⁺.

b) Alloc-pAph-Glu-((R)-1-(3-aminophenyl)ethyl)amide and Alloc-pAph-Glu-((S)-1-(3-aminophenyl)ethyl)amide To a solution of 59 mg (0.124 mmol) of Alloc-pAph-Glu(OtBu)—OH and 18 mg (0.125 mmol) of (RS)-3-(1-aminoethyl)phenylamine in 5 ml of DMF was added 41 mg (0.124 mmol) of TOTU and 28 mg (0.248 mmol) of DIEA at 3° C. After 12 h at RT the solvent was removed and the residue was treated with 1 ml of 90% TFA. After 8 h at RT the solvent was evaporated and the residue was purified by HPLC to give 0.7 mg of diastereomer I (MS=539.2 (M+1)$^+$) and 0.9 mg of diastereomer II (MS=539.2 (M+1)$^+$).

Example 9

Alloc-pAph-Glu-((R)-1-(4-aminophenyl)butyl)amide and Alloc-pAph-Glu-((S)-1-(4-aminophenyl)butyl)amide (RS)-4-(1-Aminobutyl)phenylamine was synthesized analogously to the procedure described in example 8, starting from the corresponding ketone. To a solution of 60 mg (0.126 mmol) of Alloc-pAph-Glu(OtBu)—OH and 24 mg (0.121 mmol) of (RS)-4-(1-aminobutyl)phenylamine in 5 ml of DMF was added 42 mg (0.126 mmol) of TOTU and 32 µl (0.252 mmol) of NEM at 3° C. After 12 h at RT the solvent was removed and the residue was treated with 1 ml of 90% TFA. After 8 h at RT the solvent was evaporated and the residue was purified by HPLC to give 3 mg of diastereomer I (MS=567.3 (M+1)$^+$) and 3 mg of diastereomer II (MS=567.3 (M+1)$^+$).

Example 10

Alloc-pAph-Glu-(3-(3,5-dichlorobenzenesulfonylamino)propyl)amide a) N-(3-Aminopropyl)-3,5-dichlorobenzenesulfonamide 1,3-Diaminopropane (6 g, 81.5 mmol) was dissolved in 45 ml of 1,4-dioxane, and at 15–20° C. a solution of 3,5-dichlorobenzenesulfonyl chloride (2 g, 8.15 mmol) in 5 ml of 1,4-dioxane was slowly added over 3 hours under stirring. Stirring was continued at RT. After 30 hours the formed precipitate was filtered off and the filtrate concentrated in vacuo. The residue was distributed between ethyl acetate and water. The organic layer was separated, dried with magnesium sulfate, filtered, and concentrated in vacuo to yield 2.0 g of crude material. 750 mg of this material was purified by HPLC to yield 675 mg of the title compound as TFA salt (MS=283.0 (M+H)$^+$). 200 mg of this product was dissolved in ethyl acetate and treated with 5 ml of diluted potassium carbonate solution. The organic layer was separated, dried, filtered, and concentrated in vacuo to yield the TFA free title amine.

b) Alloc-pAph-Glu-3-((3,5-dichlorobenzenesulfonylamino)propyl)amide

N-(3-Aminopropyl)-3,5-dichlorobenzenesulfonamide (7 mg, 23.4 µmol), Alloc-pAph-Glu(OtBu)—OH (10 mg, 19.5 µmol), and HOBt hydrate (9 mg, 58.5 µmol) were dissolved in 2 ml of a 1:3 mixture of DMF and DCM. Then DIC (6 µl, 39 µmol) was added. After stirring for 3 h and standing over the weekend at RT the solvent was removed and the residue was purified by HPLC to yield 6.5 mg of the coupling product. This was stirred in 4 ml of a 1:1 mixture of TFA and DCM for 2 h. After standing overnight the solvent was evaporated and the residue was dissolved in DCM. After evaporation of the solvent the residue was purified by HPLC and lyophilized to yield 3.5 mg of the title compound. MS=685.4 (M+H)$^+$.

Example 11

Alloc-pAph-Glu-(3-((naphthalene-2-sulfonylamino)methyl)benzyl)amide a) Naphthalene-2-sulfonic Acid (3-aminomethylbenzyl)amide α,α'-Diamino-m-xylene (24 g, 176 mmol) was dissolved in 50 ml 1,4-dioxane, and at 15–20° C. naphthalene-2-sulfonyl chloride (4 g, 17.6 mmol) dissolved in 50 ml of 1,4-dioxane was slowly added over 3 hours under stirring. Stirring was continued at RT. After standing overnight the formed precipitate was filtered off and the filtrate concentrated in vacuo. The residue was distributed between DCM and water. The organic layer was separated and washed with water and 1 N HCl. The oily layer formed between the organic and aqueous layer was separated. It solidified on standing. This solid material was treated with ethyl acetate, sucked off, and washed with ethyl acetate. The residue was dissolved in water and treated with potassium carbonate solution. The aqueous solution was extracted three times with ethyl acetate, and the combined organic phases were dried over magnesium sulfate, filtered, and concentrated to yield 3.2 g of the title compound. MS=327.3 (M+H)$^+$.

b) Alloc-pAph-Glu-(3-((naphthalene-2-sulfonylamino)methyl)benzyl)amide

Naphthalene-2-sulfonic acid (3-aminomethylbenzyl)amide (8 mg, 23.4 µmol), Alloc-pAph-Glu(OtBu)—OH (10 mg, 19.5 µM), and HOBt hydrate (9 mg, 58.5 µmol) were dissolved in 2 ml of a 1:3 mixture of DMF and DCM. Then DIC (6 µl, 39 µmol) was added. After 3 h the reaction mixture was concentrated and treated as described in example 10. Lyophilization gave 7.6 mg of the title compound. MS=729.4 (M+H)$^+$.

Example 12

Alloc-pAph-Glu-(4-carbamoylmethylthiazol-2-yl)amide a) Fmoc-Glu(OtBu)-(4-carbamoylmethylthiazol-2-yl)amide To a solution of 1.24 g (2.1 mmol) of Fmoc-Glu(OtBu)-OPfp in 10 ml of DMF was added a solution of 0.33 g (2.1 mmol) of 2-(2-aminothiazol-4-yl)-acetamide in 10 ml of DMF over a period of 15 min. After 2 days at RT the solvent was evaporated and the residue was washed with ether to give 0.86 g of the title compound. MS=565.4 (M+H)$^+$.

b) H-Glu(OtBu)-(4-carbamoylmethylthiazol-2-yl)amide

A solution of 0.86 g (1.52 mmol) of Fmoc-Glu(OtBu)-(4-carbamoylmethylthiazol-2-yl)amide in 5 ml of DMF/piperidine (1:1) was stirred for 3 h at RT. The solvent was evaporated and the residue was filtered through celite to give 0.37 g of the title compound. MS=343.4 (M+H)$^+$.

c) Alloc-pAph-Glu-(4-carbamoylmethylthiazol-2-yl)amide

To a solution of 50 mg (0.17 mmol) of Alloc-pAph-OH and 39.1 mg of TOTU in 10 ml of DMF was added 58.8 mg (0.17 mmol) of H-Glu(OtBu)-(4-carbamoylmethylthiazol-2-yl)amide and 21.8 µl of NEM. After 24 h at RT the solvent was removed and the residue was distributed between an aqueous solution of NaHCO$_3$ and ethyl acetate. The organic phase was dried, filtered, and evaporated. The residue was stirred for 16 h with 0.6 ml of TFA. 50 ml of ethyl acetate and 10 ml of ligroin were added and the precipitate was filtered to give 59 mg of the title compound. MS=560.4 (M+1)$^+$.

Example 13

Alloc-pAph-Glu-(4-amino-2-methylpyrimidin-5-ylmethyl)amide

To a solution of 53 mg (0.11 mmol) of Alloc-pAph-Glu (OtBu)—OH and 15 mg (0.11 mmol) of 4-amino-5-aminomethyl-2-methylpyrimidine in 5 ml of DMF was added 37 mg (0.115 mmol) of TOTU and 14 µl of NEM at 3° C. After 12 h at RT the solvent was removed and the residue was treated with 1 ml of 90% TFA. After 8 h at RT ethyl acetate, isopropanol, and methanol were added and the precipitate was filtered to give 46 mg of the title compound. MS=541.3 (M+1)$^+$.

Example 14

Alloc-pAph-Asp-(3-aminobenzyl)amide

To a solution of 50 mg (0.153 mmol) of Alloc-pAph-OH and 50.3 mg (0.153 mmol) of H-Asp(OtBu)-3-aminobenzylamide hydrochloride in 5 ml of DMF was added 50 mg (0.153 mmol) of TOTU and 60 µl of NEM at 3° C. After 12 h at RT the solvent was removed and the residue was treated with 1 ml 90% of TFA. After 8 h at RT ethyl acetate was added and the oily precipitate was separated and freeze-dried to give 82 mg of the title compound. MS=511.3 (M+1)$^+$.

Example 15

Alloc-pAph-2-Aad-(3-aminobenzyl)amide

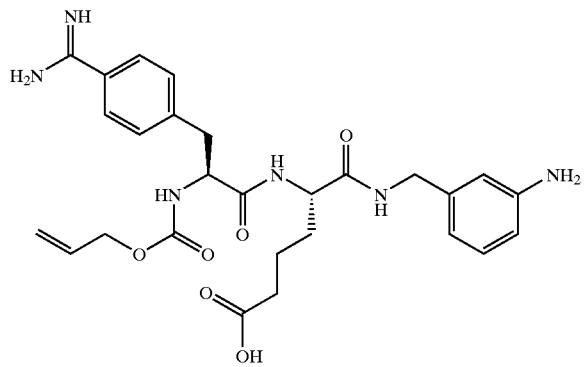

To a solution of 100 mg (0.305 mmol) of Alloc-pAph-OH hydrochloride and 139 mg (0.305 mmol) of H-2-Aad (OtBu)-(3-aminobenzyl)amide hydrochloride in 5 ml of DMF was added 128 mg (0.389 mmol) of TOTU and 150 µl of NEM at 3° C. After 16 h at RT the solvent was removed and the residue was treated with 1 ml 90% of TFA. After 8 h at RT ethyl acetate was added and the precipitate was filtered and purified by HPLC and lyophilized to give 43 mg of the title compound. MS=539.2 (M+1)$^+$.

Example 16

Alloc-pAph-Glu(OCH$_3$)-(3-aminobenzyl)amide 50 mg (0.153 mmol) of Alloc-pAph-OH hydrochloride and 75 mg (0.153 mmol) of H-Glu(OCH$_3$)-(3-aminobenzyl) amide hydrochloride were reacted according to the procedure described in example 15 to give 22 mg of the title compound. MS=539.3 (M+1)$^+$.

Analogously to the above examples the following example compounds were prepared.

Example compounds of formula Ia:

| Example | R$^a$ in formula Ia | MS |
|---|---|---|
| 17 | 3,5-dichlorophenyl | 685.4(M+1)$^+$ |
| 18 | 1-naphthyl | 729.4(M+1)$^+$ |
| 19 | 4-methoxyphenyl | 709.2(M+1)$^+$ |
| 20 | methyl | 617.1(M+1)$^+$ |
| 21 | dimethylamino | 644.1(M−1)$^+$ |
| 22 | 2-phenylethenyl | 705.2(M+1)$^+$ |
| 23 | 2-acetylamino-1,3-thiazol-5-yl | 685.4(M+1)$^+$ |
| 24 | 5-chlorothiophen-2-yl | 720.1(M+1)$^+$ |
| 25 | 4-fluorophenyl | 697.2(M+1)$^+$ |

Example compounds of formula Ib:

| Example | R$^b$ in formula Ib | MS |
|---|---|---|
| 26 | 3-bromophenyl | 697.1(M+1)$^+$ |
| 27 | 4-acetylaminophenyl | 730.3(M+1)$^+$ |
| 28 | 4-methoxyphenyl | 647.2(M+1)$^+$ |
| 29 | 4-fluorophenyl | 691.3(M+1)$^+$ |

Example compounds of formula Ic:

| Example | R$^c$ in formula Ic | MS |
|---|---|---|
| 30 | 3-bromophenyl | 723.3 (M + 1)$^+$ |
| 31 | 3-trifluoromethylphenyl | 711.1 (M + 1)$^+$ |

-continued

Ic

| Example | R$^c$ in formula Ic | MS |
|---|---|---|
| 32 | 3-chlorophenyl | 677.1 M$^+$ |
| 33 | 2,5-dichlorophenyl | 711.1 M$^+$ |
| 34 | 5-chloro-3-methoxyphenyl | 682.2 (M + 1)$^+$ |

Example 35

((S)-2-Allyloxycarbonylamino-3-(4-carbamimidoylphenyl)propionyl)-Glu-(3-(pyridin-3-ylsulfonylamino)phenyl)amide (Alloc-pAph-Glu-(3-(pyridin-3-ylsulfonylamino)phenyl)amide)

MS=652.4 (M+1)$^+$.

Example 36

((R)-2-Allyloxycarbonylamino-3-(4-carbamimidoylphenyl)propionyl)-Glu-(3-(pyridin-3-ylsulfonylamino)phenyl)amide (Alloc-D-pAph-Glu-(3-(pyridin-3-ylsulfonylamino)phenyl)amide)

MS=652.4 (M+1)$^+$.

Example compounds of formula Id:

Id

| Example | R$^d$ in formula Id | MS |
|---|---|---|
| 37 | 3-aminomethylbenzyl | 539.2(M+1)$^+$ |
| 38 | 3-aminopropyl | 477.4(M+1)$^+$ |
| 39 | 3,4-dichlorophenyl (a) | 578.2(M+1)$^+$ |
| 40 | 3-carbamimidoylbenzyl (a) | 552.2(M+1)$^+$ |
| 41 | 1-(1-naphthyl)ethyl | 574.3(M+1)$^+$ |
| 42 | 1-(6-amino-pyridin-3-yl)methyl | 526.3(M+1)$^+$ |
| 43 | 2,4-dihydroxy-pyrimidin-5-yl (a) | 530.3(M+1)$^+$ |

-continued

Id

| Example | R$^d$ in formula Id | MS |
|---|---|---|
| 44 | 1-phenyl-1-(4-pyridyl)methyl | 587.4(M+1)$^+$ |
| 45 | 1-(6-chloro-2-naphthyl)-1-(1-methyl-piperidin-4-yl)-methyl (a) | 691.3(M+1)$^+$ |
| 46 | 1,1-diphenylmethyl | 586.2(M+1)$^+$ |
| 47 | 4-cyanobenzyl | 535.4(M+1)$^+$ |
| 48 | 4-dimethylaminobenzyl | 553.1(M+1)$^+$ |
| 49 | 4-aminophenyl | 511.4(M+1)$^+$ |
| 50 | 2-(2,5-dioxo-imidazolidin-1-yl)ethyl | 546.4(M+1)$^+$ |
| 51 | 4-carbamoylbenzyl | 553.4(M+1)$^+$ |
| 52 | 1-(piperidin-4-yl)methyl | 517.5(M+1)$^+$ |
| 53 | 1-(1-hydroxycyclohexyl)methyl | 532.2(M+1)$^+$ |
| 54 | 2-(pyridin-3-yl)ethyl | 525.4(M+1)$^+$ |
| 55 | 2-carbamoyl-1-methyl-ethyl | 505.5(M+1)$^+$ |
| 56 | 4-guanidinobenzyl | 567.5(M+1)$^+$ |
| 57 | 2-carbamoyl-1-(4-chlorophenyl)-ethyl | 601.4(M+1)$^+$ |
| 58 | 1-(1-carbamimidoylpiperidin-4-yl)methyl (a) | 459.6(M+1)$^+$ |
| 59 | 3-methylbenzyl | 524.5(M+1)$^+$ |
| 60 | 3-ureidobenzyl | 568.5(M+1)$^+$ |
| 61 | (R)-1-(3-nitrophenyl)propyl | 583.2(M+1)$^+$ |
| 62 | (S)-1-(3-nitrophenyl)propyl | 583.2(M+1)$^+$ |
| 63 | 6-hydroxy-2,2-dimethylchroman-4-yl | 596.3(M+1)$^+$ |
| 64 | 4-amino-9H-fluorene-9-yl | 599.2(M+1)$^+$ |
| 65 | 3-acetylaminopropyl | 519.2(M+1)$^+$ |
| 66 | 2-(4-aminophenyl)-1-(4-methylsulfonyl-phenyl)-ethyl | 693.3(M+1)$^+$ |

(a) isolated as hydrochloride salt

Example compounds of formula Ie:

Ie

| Example | R$^e$ in formula Ie | MS |
|---|---|---|
| 67 | 3-bromophenyl | 745.1(M+1)$^+$ |
| 68 | 3-chlorophenyl | 699.3(M+1)$^+$ |
| 69 | 4-methoxyphenyl | 695.3(M+1)$^+$ |

Example 70

((S)-2-(3-Bromobenzenesulfonylamino)-3-(4-carbamimidoylphenyl)propionyl)-Glu-(3-aminobenzyl)amide MS=659.1 (M+1)$^+$.

Example 71

((S)-2-(3-Chlorobenzoylamino)-3-(4-carbamimidoylphenyl)propionyl)-Glu-(3-aminobenzyl)amide MS=579.2 (M+1)$^+$.

Pharmacological Testing

The ability of compounds of formula I to inhibit factor VIIa or other enzymes like factor Xa, thrombin, plasmin, or trypsin can be assessed by determining the concentration of the compound of formula I that inhibits enzyme activity by 50%, i.e., the IC$_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the IC$_{50}$ value is corrected for competition with substrate using the formula: Ki=IC$_{50}$/{1+(substrate concentration/Km)} wherein Km is the Michaelis-Menten constant (Chen and Prusoff, *Biochem. Pharmacol.* 22 (1973), 3099–3108; I. H. Segal, *Enzyme Kinetics*, John Wiley & Sons, New York (1975) 100–125; which are incorporated herein by reference).

a) Factor VIIa (FVIIa) Assay

The inhibitory activity (expressed as inhibition constant Ki (FVIIa)) of compounds of formula I towards factor VIIa/tissue factor activity was determined using a chromogenic assay essentially as described previously (J. A. Ostrem et al., *Biochemistry* 37 (1998) 1053–1059, which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 μl of human factor VIIa and TF (5 nM and 10 nM, respective final concentration) combined with 40 μl of inhibitor dilutions in 10% DMSOFTBS-PEG buffer (50 mM Tris, 15 mM NaCl, 5 mM CaCl$_2$, 0.05% PEG 8000, pH 8.15). Following a 15 min preincubation period, the assay was initiated by the addition of 35 μl of the chromogenic substrate S-2288 (D-Ile-Pro-Arg-p-nitroanilide, Pharmacia Hepar Inc., 500 μM final concentration).

The following test results (inhibition constants Ki (FVIIa)) were obtained.

| Example Compound | Ki (FVIIa) (μM) |
| --- | --- |
| Example 1 | 0.4 |
| Example 2 | 0.2 |
| Example 3 | 0.8 |
| Example 4 | 0.7 |
| Example 5 | 0.6 |
| Example 6 | 0.4 |
| Example 7 | 0.8 |
| Example 10 | 0.68 |
| Example 11 | 0.8 |
| Example 12 | 44.1 |
| Example 13 | 1.9 |
| Example 14 | 3.4 |
| Example 15 | 75.7 |
| Example 17 | 6.49 |
| Example 18 | 1.8 |
| Example 19 | 0.68 |
| Example 20 | 2.03 |
| Example 21 | 0.62 |
| Example 22 | 1.46 |
| Example 23 | 1.38 |
| Example 24 | 0.89 |
| Example 25 | 1.88 |
| Example 26 | 0.30 |
| Example 27 | 0.73 |
| Example 28 | 0.28 |
| Example 29 | 0.59 |
| Example 30 | 0.43 |
| Example 31 | 0.64 |
| Example 32 | 0.56 |
| Example 33 | 0.67 |
| Example 34 | 1.05 |
| Example 37 | 3.7 |
| Example 38 | 3.82 |

The following tests can serve to investigate the inhibition of selected other coagulation enzymes and other serine proteases by compounds of formula I and thus to determine their specificity.

b) Factor Xa Assay

TBS-PEG buffer (50 mM Tris-Cl, pH 7.8,200 mM NaCl, 0.05% (w/v) PEG-8000, 0.02% (w/v) NaN$_3$) is used for this assay. The IC$_{50}$ is determined by combining in appropriate wells of a Costar half-area microtiter plate 25 μl human factor Xa (Enzyme Research Laboratories, Inc.; South Bend, Ind.) in TBS-PEG; 40 μl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay is performed by pre-incubating the compound of formula I plus enzyme for 10 min. Then the assay is initiated by adding substrate to obtain a final volume of 100 μl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The enzyme concentration is 0.5 nM and substrate concentration is 140 μM.

c) Thrombin Assay

TBS-PEG buffer is used for this assay. The IC$_{50}$ is determined as above for the factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend, Ind.). The enzyme concentration is 175 μM.

d) Plasmin Assay

TBS-PEG buffer is used for this assay. The IC$_{50}$ is determined as described above for the factor Xa assay, except that the substrate is S-2251 (D-Val-L-Leu-L-Lys-p-nitroanilide; Kabi) and the enzyme is human plasmin (Kabi). The enzyme concentration is 5 nM and the substrate concentration is 300 μM.

e) Trypsin Assay

TBS-PEG buffer containing 10 mM CaCl$_2$ is used for this assay. The IC$_{50}$ is determined as described above in the factor Xa assay, except that the substrate is BAPNA (benzoyl-L-Arg-p-nitroanilide; Sigma Chemical Co.; St. Louis, Mo.) and the enzyme is bovine pancreatic trypsin (Type XIII, TPCK treated; Sigma). The enzyme concentration is 50 nM and the substrate concentration is 300 μM.

Rat Arteriovenous Shunt Model of Thrombosis

The antithrombotic efficacy of compounds of the invention can be assessed using rat extracorporeal arteriovenous (AV) shunt. The AV shunt circuit consists of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

The test compound is administered by continuous infusion into the tail vein using a syringe pump and butterfly catheter. The compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats, which are infused with saline.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A compound of formula I,

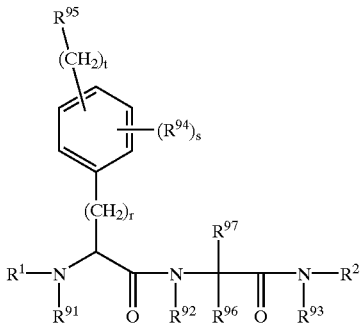

wherein:
r is 0, 1, 2, or 3;
s is 0, 1, 2, 3, or 4;
t is 0, 1, or 2;
$R^1$ is selected from hydrogen, $R^{11}$—CO—, and $R^{12}$—$SO_2$—;
$R^{11}$ is selected from $(C_1-C_8)$-alkyl, $(C_6-C_{14})$-aryl, $(C_6-C_{14})$-aryl-$(C_1-C_4)$-alkyl-, Het-, Het-$(C_1-C_4)$-alkyl-, $(C_1-C_8)$-alkyloxy-, $(C_6-C_{14})$-aryloxy-, $(C_6-C_{14})$-aryl-$(C_1-C_4)$-alkyloxy-, amino, $(C_1-C_8)$-alkylamino-, $(C_6-C_{14})$-arylamino-, and $(C_6-C_{14})$-aryl-$(C_1-C_4)$-alkylamino-, where all these groups are unsubstituted or substituted by one or more identical or different $R^{40}$ substituents or $R^{11}$ is hydrogen;
$R^{12}$ is selected from $(C_1-C_8)$-alkyl, $(C_6-C_{14})$-aryl, $(C_6-C_{14})$-aryl-$(C_1-C_4)$-alkyl- Het-, Het-$(C_1-C_4)$-alkyl-, di$((C_1-C_8)$-alkyl)amino-, and di$((C_6-C_{14})$-aryl-$(C_1-C_4)$-alkyl)amino-, where all these groups are unsubstituted or substituted by one or more identical or different $R^{40}$ substituents;

$R^2$ is hydrogen $R^{21}(R^{22})$CH—, $R^{23}$—Het-$(CH_2)_k$—, $R^{23}(R^{24})$N—$(CH_2)_m$—D—$(CH_2)_n$—, or $R^{25}(R^{26})$N—CO—$(CH_2)_p$—D—$(CH_2)_q$—, wherein D is a divalent —$C(R^{31})(R^{32})$— residue, a divalent $(C_6-C_{14})$-arylene residue, or a divalent residue of an aromatic Het group containing 5 to 10 ring atoms of which 1, 2, 3, or 4 are identical or different ring heteroatoms selected from nitrogen, oxygen, and sulfur, and the numbers k, m, n, p, and q which are independent of each other and can be identical or different are 0, 1, 2, 3, 4, or 5, with the proviso that when D is —$C(R^{31})(R^{32})$—, the sum m+n cannot be 0 and the sum p+q cannot be 0;

$R^{21}$ and $R^{22}$ which are independent of each other and can be identical or different are selected from hydrogen, $(C_1-C_{12})$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different substituents selected from $R^{40}$, $(C_1-C_8)$-alkylamino-, di-$((C_1-C_8)$-alkyl)-amino-, $(C_6-C_{14})$-aryl-$(C_1-C_4)$-alkylamino-, $(C_6-C_{14})$-arylamino-, aminocarbonyl-, and aminocarbonyl-$(C_1-C_8)$-alkyl-, or $R^{21}$ and $R^{22}$ together with the carbon atom to which they are bonded form a saturated or unsaturated 3-membered to 8-membered carbocyclic ring which can be condensed to one or two ring systems which are heteroaromatic rings containing 5 to 10 ring atoms of which 1, 2, or 3 are identical or different heteroatoms selected from nitrogen, oxygen, and sulfur, and/or $(C_6-C_{10})$ carbocyclic aromatic rings, where the resulting $R^{21}(R^{22})$CH— group is unsubstituted or substituted by one or more identical or different substituents selected from $R^{40}$, $(C_1-C_8)$-alkylamino-, di-$((C_1-C_8)$-alkyl)-amino-, $(C_6-C_{14})$-aryl-$(C_1-C_4)$-alkylamino-, $(C_6-C_{14})$-arylamino-, aminocarbonyl-, and aminocarbonyl-$(C_1-C_8)$-alkyl-;

$R^{23}$ is hydrogen, $R^{27}$—$SO_2$—, or $R^{28}$—CO—;
$R^{24}$ is selected from hydrogen, $(C_1-C_8)$-alkyl, $(C_6-C_{14})$-aryl, and $(C_6-C_{14})$-aryl-$(C_1-C_4)$-alkyl-;
$R^{25}$ and $R^{26}$ which are independent of each other and can be identical or different are selected from hydrogen, $(C_1-C_8)$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different $R^{40}$ substituents;
$R^{27}$ is selected from $(C_1-C_8)$-alkyl, $(C_6-C_{14})$-aryl, $(C_6-C_{14})$-aryl-$(C_1-C_4)$-alkyl-, Het-, $(C_1-C_4)$-alkyl-, amino, $(C_1-C_8)$-alkylamino-, di-$((C_1-C_8)$-alkyl)amino-, $(C_6-C_{14})$-arylamino-, and $(C_6-C_{14})$-aryl-$(C_1-C_4)$-alkylamino-, where all these groups are unsubstituted or substituted by one or more identical or different $R^{40}$ substituents;
$R^{28}$ is selected from $R^{27}$, $(C_1-C_8)$-alkyloxy-, $(C_6-C_{14})$-aryloxy-, and $(C_6-C_{14})$-aryl-$(C_1-C_4)$-alkyloxy-, where all these groups are unsubstituted or substituted by one or more identical or different $R^{40}$ substituents;
$R^{31}$ and $R^{32}$ which are independent of each other and can be identical or different are selected from hydrogen, $(C_1-C_{12})$-alkyl, $(C_6-C_{14})$-aryl, $(C_6-C_{14})$-aryl-$(C_1-C_4)$-alkyl-, Het-, and Het-$(C_1-C_4)$-alkyl-, where all these groups are unsubstituted or substituted by one or more identical or different $R^{40}$ substituents;
$R^{40}$ is selected from halogen, hydroxy, $(C_1-C_8)$-alkyloxy-, $(C_6-C_{14})$-aryl-$(C_1-C_8)$-alkyloxy-, $(C_6-C_{14})$-aryloxy-, $(C_1-C_8)$-alkyl, $(C_6-C_{14})$-aryl, $(C_6-C_{14})$-aryl-$(C_1-C_8)$-alkyl-, $(C_1-C_8)$-alkylsulfonyl-, trifluoromethyl, acetylamino-, amino, amidino, guanidino, oxo, nitro, and cyano, where the $R^{40}$ groups are independent of each other and can be identical or different;

$R^{91}$, $R^{92}$, and $R^{93}$ which are independent of each other and can be identical or different are selected from hydrogen, $(C_1-C_8)$-alkyl, $(C_6-C_{14})$-aryl, $(C_6-C_{14})$-aryl-$(C_1-C_4)$-alkyl-, Het-, and Het-$(C_1-C_4)$-alkyl-;

$R^{94}$ is selected from $(C_1-C_4)$-alkyl, $(C_6-C_{14})$-aryl, amino, nitro, halogen, trifluoromethyl, hydroxy, and $(C_1-C_4)$-alkyloxy-, where the $R^{94}$ groups are independent of each other and can be identical or different; $R^{95}$ is selected from amidino, guanidino, $((C_1-C_4)$-alkyl$)$oxycarbonylamidino-, $((C_1-C_4)$-alkyl$)$oxycarbonylguanidino-, and hydroxyamidino-;

$R^{96}$ is selected from hydrogen, $R^{98}$—$(C_1-C_8)$-alkyl-, $R^{98}$-$(C_6-C_{14})$-aryl-, $R^{98}$—$(C_6-C_{14})$-aryl-$(C_1-C_4)$-alkyl-, $R^{98}$—Het-, and $R^{98}$—Het-$(C_1-C_4)$-alkyl-;

$R^{97}$ is selected from $R^{99}$—$(C_1-C_8)$-alkyl-, $R^{99}$—$(C_6-C_{14})$-aryl-, $R^{99}$—$(C_6-C_{14})$-aryl-$(C_1-C_4)$-alkyl-, $R^{99}$—Het-, and $R^{99}$—Het-$(C_1-C_4)$-alkyl-;

$R^{98}$ and $R^{99}$ which are independent of each other and can be identical or different are selected from hydroxycarbonyl-, $(C_1-C_8)$-alkyloxycarbonyl-, $(C_6-C_{14})$-aryloxycarbonyl-, $(C_6-C_{14})$-aryl-$(C_1-C_4)$-alkyloxycarbonyl-, aminocarbonyl-, $(C_1-C_8)$-alkylaminocarbonyl-, tetrazolyl, —P(O)(OH)$_2$, —S(O)$_2$OH, and —S(O)$_2$NH$_2$;

Het is a saturated, partially unsaturated, or aromatic monocyclic or bicyclic heterocyclic ring system containing 3 to 10 ring atoms of which 1, 2, 3, or 4 are identical or different heteroatoms selected from nitrogen, oxygen, and sulfur; or a stereoisomer of formula I, or a salt of formula I, or mixtures of any of the foregoing.

2. A compound of claim 1, in which $R^{11}$ is $(C_1-C_8)$-alkyl, $(C_6-C_{10})$-aryl, or $(C_1-C_8)$-alkyloxy.

3. A compound of claim 1, in which r is 0 or 1, t is 0 or 1, s is 0, 1, or 2, and $R^{95}$ is amidino, $((C_1-C_4)$-alkyl$)$oxycarbonylamidino, or hydroxyamidino.

4. A compound of claim 1, in which $R^{96}$ is hydrogen and $R^{97}$ is $R^{99}$—$(C_1-C_8)$-alkyl, wherein $R^{99}$ is hydroxycarbonyl-, $(C_1-C_8)$-alkyloxycarbonyl-, $(C_6-C_{14})$-aryl-$(C_1-C_4)$-alkyloxycarbonyl-, aminocarbonyl-, or $(C_1-C_8)$-alkylaminocarbonyl.

5. A compound of claim 1, in which $R^2$ is $R^{21}(R^{22})$CH—, $R^{23}$—Het-$(CH_2)_k$—, or $R^{23}(R^{24})$N—$(CH_2)_m$—D—$(CH_2)_n$—, wherein D is a divalent —C$(R^{31})(R^{32})$— residue, a divalent phenylene residue, or a divalent residue derived from an aromatic monocyclic Het group.

6. A compound of claim 1, in which:

r is 1;

s is 0 or 1;

t is 0;

$R^1$ is allyloxycarbonyl-;

$R^2$ $R^{21}(R^{22})$CH—, $R^{23}$—Het-$(CH_2)_k$—, or $R^{23}(R^{24})$N—$(CH_2)_m$—D—$(CH_2)_n$—;

D is a divalent —C$(R^{31})(R^{32})$— residue, a divalent phenylene residue, or a divalent residue derived from an aromatic monocyclic Het group;

$R^{94}$ is halogen;

$R^{95}$ is amidino or $((C_1-C_4)$-alkyl$)$oxycarbonylamidino- and is bonded in the 4-position of the phenyl ring in formula I;

$R^{91}$, $R^{92}$, $R^{93}$, and $R^{96}$ are hydrogen;

$R^{97}$ is $R^{99}$—CH$_2$—CH$_2$—;

$R^{99}$ is hydroxycarbonyl- or $((C_1-C_4)$-alkyl$)$oxycarbonyl-.

7. A composition, comprising at least one compound of claim 1 and a pharmaceutically acceptable carrier.

8. A composition for inhibiting factor VIIa, comprising an effective amount of at least one compound of claim 1 and a pharmaceutically acceptable carrier.

9. A method of inhibiting factor VIIa, comprising administering to a patient in need thereof a compound of claim 1 under conditions effective to inhibit factor VIIa.

10. A method of inhibiting factor VIIa, comprising contacting factor VIIa with a compound of claim 1 under conditions effective to inhibit factor VIIa.

11. A method of inhibiting the process of blood clotting, comprising administering to a patient in need thereof a compound of claim 1 under conditions effective to inhibit the blood clotting process.

12. A method of mitigating the formation of blood clots, comprising administering to a patient in need thereof a compound of claim 1 under conditions effective to mitigate the formation of blood clots.

* * * * *

UNITED STATES PATENT AND TRADEMARK OFFICE
CERTIFICATE OF CORRECTION

PATENT NO. : 6,500,803 B1
DATED : December 31, 2002
INVENTOR(S) : Klingler et al.

It is certified that error appears in the above-identified patent and that said Letters Patent is hereby corrected as shown below:

Column 43,
Line 63, after "$(C_6\text{-}C_{14})$-aryl-$(C_1\text{-}C_4)$-alkyl-", insert a comma.

Column 44,
Line 1, after "hydrogen", insert a comma.
Line 47, "Het-,$(C_1\text{-}C_4)$-alkyl-," should read -- Het-, Het-$(C_1\text{-}C_4)$-alkyl-, --.

Column 45,
Line 37, "$(C_1\text{-}C_8)$-alkyloxy." should read -- $(C_1\text{-}C_8)$-alkyloxy-. --.

Column 46,
Line 12, after "$R^2$", insert -- is --.

Signed and Sealed this

Twenty-ninth Day of July, 2003

JAMES E. ROGAN
*Director of the United States Patent and Trademark Office*